(12) United States Patent
Rao et al.

(10) Patent No.: US 6,905,877 B1
(45) Date of Patent: Jun. 14, 2005

(54) COMPOSITIONS AND METHODS FOR ALTERING AMINO ACID CONTENT OF PROTEINS

(75) Inventors: A. Gururaj Rao, Urbandale, IA (US); Heidi Major Sleister, Ankeny, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 09/478,598

(22) Filed: Jan. 6, 2000

Related U.S. Application Data

(62) Division of application No. 08/988,015, filed on Dec. 10, 1997, now abandoned.

(51) Int. Cl.[7] .................................................. C12N 15/00
(52) U.S. Cl. .................................... 435/440; 435/69.1
(58) Field of Search ................................ 435/69.1, 440

(56) References Cited

U.S. PATENT DOCUMENTS

| | | | |
|---|---|---|---|
| 5,288,629 A | * | 2/1994 | Berkner |
| 5,559,223 A | * | 9/1996 | Falco et al. |
| 5,589,615 A | | 12/1996 | De Clercq et al. |
| 6,080,913 A | | 6/2000 | Tarczynski |

FOREIGN PATENT DOCUMENTS

| | | |
|---|---|---|
| WO | WO 93/08682 | 5/1993 |
| WO | WO 94/16088 | 7/1994 |
| WO | WO 95/22625 | 8/1995 |
| WO | WO 95/31554 | 11/1995 |
| WO | WO 96/38563 | 12/1996 |
| WO | WO 97/20078 | 6/1997 |
| WO | WO 97/35023 | 9/1997 |

OTHER PUBLICATIONS

Dyer et al. Extensive Modifications for Methionine Enhancement in the beta–Barrels Do Not Alter the Structural Stability of the Bean Seed Storage Protein Phaseolin. J. Protein Chemistry (1995) 14(8):665–678.*
Goldberg ME. Investigating protein conformation, dynamics and folding with monoclonal antibodies. TIBS (1991) 16(10):358–362.*
Arnold et al. Optimizing industrial enzymes by directed evolution. Adv. Biochem. Eng. Biotechnol. (1997) 58:1–14.*
Lopes et al. Approaches for enhancing the lysine content of maize seed. Biotechnol. Nutr. Proc. Int. Symp., 3rd (1992) 237–252.*
Jaynes JM. De novo designed synthetic plant storage proteins: Enhancing protein quality of plants for improved human and animal nutrition.Biotechnology in the Feed Industry, Proceedings of Alltech's 10th Annual Symposium, Lexington, KY, May 1994, 129–153.*

Bendayan, S., et al., *The Journal of Histochemistry and Cytochemistry*, 1995, pp. 881–886, vol. 43(9).

Gordon–Kamm, et al., *The Plant Cell,* 1990, pp. 603–608, vol. 2.

Altenbach et al., Enhancement of the Methionine Content of Seed Proteins by the Expression of a Chimeric Gene Encoding a Methionine–Rich Protein in Transgenic Plants, Plant Molecular Biology, 1989, pp. 513–522, vol. 13, Belgium.

Scott et al., Searching for Peptide Ligands with an Epitope Library, Science, 1990, pp. 386–390, vol. 249.

Staswick, P., Novel Regulation of Vegetative Storage Protein Genes, The Plant Cell, Jan. 1990, pp. 1–6, vol. 2.

Stemmer, W., Rapid Evolution of a Protein In Vitro By DNA Shuffling, Nature, Aug. 4, 1994, pp. 389–391, vol. 374.

Stemmer, W., DNA Shuffling by Random Fragmentation and Reassembly: In Vitro Recombination for Molecular Evolution, Proc. Natl. Acad. Sci. USA, Oct. 1994, pp. 10747–10751, vol. 91.

Hongdi et al., A Phage Display System for Studying the Sequence Determinations of Protein Folding, Protein Science, 1995, pp. 1108–1117, vol. 4.

Marcellino et al., Modified 2S Albumins with Improved Tryptophan Content are Correctly Expressed in Transgenic Tobacco Plants, FEBS Letters, 1996, pp. 154–158, vol. 385.

Molvig et al., Enhanced Methionine Levels and Increased nutritive Value of Seeds of Transgenic Lupins (*Lupinus Angustfolius* L.) Expressing a Sunflower Seed Albumin Gene, Proc. Natl. Acad. Sci. USA, Aug. 1997, pp. 8393–8398, vol. 94, Agricultural Sciences.

Friguet et al., Immunochemical Analysis of Protein Conformation, Protein Structure a Practical Approach, pp. 287–310, IRL Press, Oxford University Press, MRC Laboratory of Molecular Biology, Hills Road, Cambridge CB2 2QH, UK.

* cited by examiner

*Primary Examiner*—Kathleen Kerr
(74) *Attorney, Agent, or Firm*—Alston & Bird LLP

(57) ABSTRACT

Methods and compositions for altering amino acid composition of a protein of interest are provided, particularly proteins whose three-dimensional structure is unknown. The method comprises creating interacting molecules to the native protein and selecting for engineered proteins which retain the native conformation by antibody binding. In this manner, the levels of essential amino acids in a protein can be increased yet the biological activity of the protein maintained. Also provided is an exemplary plant protein—*Glycine max* vegetative storage protein (VSP)—in which methionine levels have been increased.

6 Claims, 9 Drawing Sheets

VSP HOMOLOGIES

|         | 1                              | 5           | 10          | 15          | 20          | 25          | 30 |
|---------|--------------------------------|-------------|-------------|-------------|-------------|-------------|----|
| VSP-b   | R S S E V K C A S F R L A V E A H N I R A F K T I P E E C V |
| VSP-a   | R T P E V K C A S W R L A V E A H N I F G F E T I P E E C V |
| T.phos  | · · · L K C T T W R F V V E I N N L S P W K T I P E E C A |
| Ph.vulg | S D T E V R C A S W R L A V E A Q N I F G F E T I P Q Q C V |
| Ar.VSP  | · · · P N C R S W H L G F E T S N M I N F D T V P A N C K |
| Ar.1A-1 | S I N Y P N C R S W H L G V E T S N I I N F D T V P A N C K |
| Ar17A-1 | S I N Y A N C R S W H L G V E T S N I I Q F D T V P A N C K |

|         | 31          | 35          | 40          | 45          | 50          | 55 |
|---------|-------------|-------------|-------------|-------------|-------------|----|
| VSP-b   | E P T K D Y · I N G E C F R S D S K T V N Q Q A F F Y A S E |
| VSP-a   | E A T K E Y · I H G E C Y R S D S K T V N Q Q A Y F Y A R D |
| T.phos  | D Y V K E Y · M V G P G Y K M E I D R V S D E A G E Y A K S |
| Ph.vulg | D A T A N Y · I E G G Q Y R S D S K T V N Q Q I Y F A R D |
| Ar.VSP  | A Y V E D Y L I T S K Q Y C Y D S K T V N K E A Y F Y A K G |
| Ar.1A-1 | A Y V E D Y L I T S K Q Y C Y D S K T V N K E A Y F Y A K G |
| Ar17A-1 | D Y V E D Y L I T S K Q Y C Y D S K T V C K E A Y F Y A K G |

|         | 60          | 65          | 70          | 75          | 80          | 85 |
|---------|-------------|-------------|-------------|-------------|-------------|----|
| VSP-b   | R E V · H H N D I F F F G L D N T V L S N I P Y Y E K H G |
| VSP-a   | L E V · H P K D T F V F S I D N T V L S N I P Y Y K K H G |
| T.phos  | V D L G D D G R D V W I F D V D E T L L S N L P Y Y S D H R |
| Ph.vulg | R H V · H E N D V I L E N I D G T A L S N I P Y Y S Q H G |
| Ar.VSP  | L A L K N D T I N V W I F D L D D T L L S S I P Y Y A K Y G |
| Ar.1A-1 | L A L K N D T V N V W I F D L D D T L L S S I P Y Y A K Y G |
| Ar17A-1 | L A L K N D T V N V W I F D L D D T L L S S I P Y Y A K Y G |

|         | 90          | 95          | 100         | 105         | 110         | 115 |
|---------|-------------|-------------|-------------|-------------|-------------|-----|
| VSP-b   | Y G V E E F N E T L Y D E W V N K G D · A P A L P E T L K N |
| VSP-a   | Y G V E K F N S T L Y D E W V N K G N · A P A L P E T L K N |
| T.phos  | Y G L E V F D D V E F D K W V E N G T · A P A L G S S L K L |
| Ph.vulg | Y G S E K F D S E R Y D E E F V N K G E A P A L P E T L K N |
| Ar.VSP  | Y G T E N T A A G A Y W S W L V S G E · T P G L P E T L H L |
| Ar.1A-1 | Y G T E N T A P G A Y W S W L E S G E S T P G L P E T L Y L |
| Ar17A-1 | Y G T E K T D P G A Y W L W I G T G A S T P G L P E G L Y L |

FROM FIG. 1A.

|  | 120 | 125 | 130 | 135 | 140 | 145 |
|---|---|---|---|---|---|---|
| VSP-b | YNKLSLGFKIV | FSGRY | LKMAV | TEANLK |  |  |
| VSP-a | YNKLVSLGFKII | FLSGRT | LKQAV | TEANLK |  |  |
| T.phos | YQEVLKLGFKVFL | LTGRSERHRSV | TVENLM |  |  |  |
| Ph.vulg | YNKLVSLGYKII | ELSGRL | KDKRAV | TEANLK |  |  |
| Ar.VSP | YENLLELGIEP | IIISDRWKKLSEI | IIENLK |  |  |  |
| Ar.1A-1 | YENLLELGIEP | IIISDRWKKLSEV | TVENLK |  |  |  |
| Ar17A-1 | YQNIIIEVGIEP | IIISVRW | KLWKNVTLNLE |  |  |  |

|  | 150 | 155 | 160 | 165 | 170 | 175 |
|---|---|---|---|---|---|---|
| VSP-b | KAGFHTWEQ | LILKDPH | LII | ENALSYKSAM |  |  |
| VSP-a | KAGYHTWEK | LILKDPG | PSTENAVSYKTAA |  |  |  |
| T.phos | NAGFHDWHK | LILRGSD | H | GKTATTYKSER |  |  |
| Ph.vulg | KAGYNTWEK | LILKDPS | NSAEN | VVYKTAE |  |  |
| Ar.VSP | AVGVTKWKHV | LLKPNG | KLTQ | VVYKSKV |  |  |
| Ar.1A-1 | AVGVTKWKHL | LLKPNGSKLTQ | VVYKSKV |  |  |  |
| Ar17A-1 | AAGVTYWKHL | LLKPNGSNERQ | VVYKSKV |  |  |  |

|  | 180 | 185 | 190 | 195 | 200 | 205 |
|---|---|---|---|---|---|---|
| VSP-b | RENLLRQGYR | IVGIIGDQWSDLLGDHRGES |  |  |  |  |
| VSP-a | REKLIRQGYN | IVGIIGDQWSDLLGGHRGES |  |  |  |  |
| T.phos | RNAMVEEGFR | IVGNSGDQWSDLLGSSMS | Y |  |  |  |
| Ph.vulg | RAKEVQEGYR | IVGNIGDQWNDLKGENRA I |  |  |  |  |
| Ar.VSP | RNSLVRQGYN | IVGIIGDQWADLVEDTPG |  |  |  |  |
| Ar.1A-1 | RNSLVKKGYN | IVGNIGDQWADLVEDTPG |  |  |  |  |
| Ar17A-1 | RNKLVKKGYN | IVGNIGDQWADLVEDTPG |  |  |  |  |

|  | 210 | 218 |
|---|---|---|
| VSP-b | RTFKLPNPMYY | IE |
| VSP-a | RTFKLPNPLYY | IQ |
| T.phos | RSFKLPNPMYY | IL |
| Ph.vulg | RSFKLPNPMYY | TK |
| Ar.VSP | RVFKLPNPLYY | VPS |
| Ar.1A-1 | RVFKLPNPLYY | VPS |
| Ar17A-1 | RVFKLPNPLYY | VPS |

FIG. 1B.

PROPOSED VSPβ METHIONINE-ENRICHED VARIANTS

| Position | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|
| VSPβ | R | S | S | E | V | K | C | A | S | F | R | L | A | V | E | A | H | N | I | R | A | F | K | T | I | I | P | E | E | V |
| VSPβ-Met10 |   |   |   |   | M |   |   |   |   |   |   |   |   |   |   |   |   |   |   | M |   |   |   |   |   |   |   |   |   | M |
| VSPβ-Met20 |   |   |   |   | M |   |   |   |   |   |   |   |   |   |   |   |   |   |   | M |   |   |   |   |   |   |   |   |   | M |
| VSPβ-Met30 |   |   |   |   | M |   |   |   |   |   |   |   |   |   |   |   |   |   |   | M |   |   |   |   | M |   |   |   |   | M |

| Position | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 |
|---|---|---|---|---|---|---|---|---|---|---|---|---|---|---|---|---|---|---|---|---|---|---|---|---|---|---|---|---|---|---|
| VSPβ | E | P | T | K | D | Y | I | N | G | E | Q | F | R | S | D | S | K | T | D | N | Q | Q | A | F | F | Y | A | S | E | R |
| VSPβ-Met10 |   |   |   | M |   |   |   |   |   | M |   |   |   |   |   |   |   |   |   |   |   |   |   |   |   |   |   |   |   | M |
| VSPβ-Met20 | M |   |   | M |   |   |   |   |   | M |   |   |   |   |   |   |   |   |   |   |   |   |   |   |   |   |   |   |   | M |
| VSPβ-Met30 | M |   |   | M |   |   |   |   |   | M |   |   |   |   | M |   |   |   |   |   |   |   |   |   |   |   |   |   |   | M |

| Position | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 | 89 | 90 |
|---|---|---|---|---|---|---|---|---|---|---|---|---|---|---|---|---|---|---|---|---|---|---|---|---|---|---|---|---|---|---|
| VSPβ | E | V | H | H | N | D | I | F | I | F | G | I | D | N | T | V | L | S | N | I | P | Y | Y | E | K | H | G | Y | G | V |
| VSPβ-Met10 | M |   |   |   | M |   |   |   |   | M |   | M |   |   |   |   |   |   |   |   |   |   |   |   |   |   |   |   |   |   |
| VSPβ-Met20 | M |   | M |   | M |   |   |   |   |   |   | M |   |   | M |   |   |   |   |   |   |   |   |   |   |   |   |   |   | M |
| VSPβ-Met30 | M |   | M |   | M |   |   |   |   | M |   | M |   |   |   | M |   |   |   | M |   |   |   |   |   |   |   |   |   | M |

| Position | 91 | 92 | 93 | 94 | 95 | 96 | 97 | 98 | 99 | 100 | 101 | 102 | 103 | 104 | 105 | 106 | 107 | 108 | 109 | 110 | 111 | 112 | 113 | 114 | 115 | 116 | 117 | 118 | 119 | 120 |
|---|---|---|---|---|---|---|---|---|---|---|---|---|---|---|---|---|---|---|---|---|---|---|---|---|---|---|---|---|---|---|
| VSPβ | E | E | F | N | E | T | L | Y | D | E | W | V | N | K | G | D | A | P | A | L | P | E | T | L | K | N | Y | N | K | L |
| VSPβ-Met10 |   |   |   |   |   |   |   |   |   |   |   |   |   |   |   |   |   |   |   |   |   |   |   |   |   |   |   |   |   |   |
| VSPβ-Met20 |   |   |   |   |   |   | M |   |   |   | M |   |   |   |   |   |   |   |   |   |   |   |   |   |   |   |   |   |   |   |
| VSPβ-Met30 |   |   | M |   | M |   | M |   |   |   |   |   |   |   |   |   |   |   |   |   |   |   |   |   |   |   |   |   |   |   |

| Position | 121 | 122 | 123 | 124 | 125 | 126 | 127 | 128 | 129 | 130 | 131 | 132 | 133 | 134 | 135 | 136 | 137 | 138 | 139 | 140 | 141 | 142 | 143 | 144 | 145 | 146 | 147 | 148 | 149 | 150 |
|---|---|---|---|---|---|---|---|---|---|---|---|---|---|---|---|---|---|---|---|---|---|---|---|---|---|---|---|---|---|---|
| VSPβ | L | S | L | G | F | K | I | V | F | L | S | G | R | Y | L | D | K | M | A | V | T | E | A | N | L | K | K | A | G | F |
| VSPβ-Met10 | M |   |   |   |   | M |   |   |   |   |   |   |   |   |   |   |   | M |   |   |   |   |   |   |   | M |   |   |   |   |
| VSPβ-Met20 | M |   |   |   |   | M |   |   |   | M |   |   |   |   |   |   |   | M |   |   |   |   |   |   |   | M |   |   |   | M |
| VSPβ-Met30 | M |   |   |   |   | M |   |   |   | M |   |   | M |   |   |   |   | M |   |   |   |   |   |   |   | M |   |   |   | M |

| Position | 151 | 152 | 153 | 154 | 155 | 156 | 157 | 158 | 159 | 160 | 161 | 162 | 163 | 164 | 165 | 166 | 167 | 168 | 169 | 170 | 171 | 172 | 173 | 174 | 175 | 176 | 177 | 178 | 179 | 180 |
|---|---|---|---|---|---|---|---|---|---|---|---|---|---|---|---|---|---|---|---|---|---|---|---|---|---|---|---|---|---|---|
| VSPβ | H | T | W | E | Q | L | I | L | K | D | P | H | L | I | T | P | N | A | L | S | Y | K | S | A | M | R | E | N | L | L |
| VSPβ-Met10 |   |   |   |   |   |   |   |   |   |   |   |   |   |   |   |   |   |   |   |   |   |   |   |   | M |   |   |   | L |   |
| VSPβ-Met20 |   |   |   |   |   |   |   |   |   |   |   |   |   | M |   |   | M |   |   |   |   |   |   |   | M |   |   |   | M |   |
| VSPβ-Met30 |   |   |   |   |   |   |   | M |   |   | M | M |   |   | M |   |   |   |   |   |   |   |   |   | M |   |   |   | M |   |

| Position | 181 | 182 | 183 | 184 | 185 | 186 | 187 | 188 | 189 | 190 | 191 | 192 | 193 | 194 | 195 | 196 | 197 | 198 | 199 | 200 | 201 | 202 | 203 | 204 | 205 | 206 | 207 | 208 | 209 | 210 |
|---|---|---|---|---|---|---|---|---|---|---|---|---|---|---|---|---|---|---|---|---|---|---|---|---|---|---|---|---|---|---|
| VSPβ | R | Q | G | Y | R | I | V | G | I | I | G | D | Q | W | S | D | L | L | G | D | H | R | G | E | S | R | T | F | K | L |
| VSPβ-Met10 |   |   |   |   |   |   | M |   |   |   |   |   |   |   |   |   |   |   |   |   | M |   |   |   |   |   |   |   |   |   |
| VSPβ-Met20 |   |   |   |   |   |   | M |   |   |   |   |   |   |   |   |   |   | M |   |   | M |   |   |   |   | M |   |   |   |   |
| VSPβ-Met30 |   |   |   |   |   |   | M |   |   |   |   |   |   |   |   |   |   |   |   |   | M |   |   | M |   | M |   |   |   | M |

| Position | 211 | 212 | 213 | 214 | 215 | 216 | 217 | 218 |
|---|---|---|---|---|---|---|---|---|
| VSPβ | P | N | P | M | Y | Y | I | E |
| VSPβ-Met10 |   |   |   | M | M |   |   |   |
| VSPβ-Met20 |   |   |   | M | M |   |   |   |
| VSPβ-Met30 |   |   |   | M | M |   |   |   |

FIG. 2.

VSPβ-met10 sequence

```
       SfiI
  1    GGCCCAGCCGGCCAGATCTTCGGAGATGAAATGCGCTAGCTTTAGGCTTGCTGTGGAAGC   60
       CCGGGTCGGCCGGTCTAGAAGCCTCTACTTTACGCGATCGAAATCCGAACGACACCTTCG

61    ACACAACATGCGAGCCTTTAAAACCATTCCTGAAGAGTGCATGGAACCAACAAAGGACTA  120
       TGTGTTGTACGCTCGGAAATTTTGGTAAGGACTTCTCACGTACCTTGGTTGTTTCCTGAT

121    CATGAATGGCGAACAATTTCGAATGGACTCTAAAACAGTTAACCAACAGGCCTTCTTTTA  180
       GTACTTACCGCTTGTTAAAGCTTACCTGAGATTTTGTCAATTGGTTGTCCGGAAGAAAAT

181    TGCTAGTGAAATGGAAATGCATCACAACGACATGTTTATATTCGGCATGGATAACACCAT  240
       ACGATCACTTTACCTTTACGTAGTGTTGCTGTACAAATATAAGCCGTACCTATTGTGGTA

241    GCTCTCTAATATCCCATACTATGAAAAACATGGATATGGGGTGGAGGAATTTAATGAAAC  300
       CGAGAGATTATAGGGTATGATACTTTTTGTACCTATACCCCACCTCCTTAAATTACTTTG

301    CTTATATGATGAATGGGTTAACAAGGGCGACGCACCGGCATTGCCAGAGACTCTTAAAAA  360
       GAATATACTACTTACCCAATTGTTCCCGCTGCGTGGCCGTAACGGTCTCTGAGAATTTTT

361    TTACAACAAGCTGATGTCCCTTGGCTTCAAGATGGTATTCTTGTCAGGAAGGTACCTTGA  420
       AATGTTGTTCGACTACAGGGAACCGAAGTTCTACCATAAGAACAGTCCTTCCATGGAACT

421    CAAAATGGCCGTAACAGAAGCAAACCTAATGAAGGCTGGCTTCCACACATGGGAGCAGTT  480
       GTTTTACCGGCATTGTCTTCGTTTGGATTACTTCCGACCGAAGGTGTGTACCCTCGTCAA

481    AATTCTCAAGGATCCACATCTTATGACTCCAAATGCACTTTCATACAAATCAGCAATGAG  540
       TTAAGAGTTCCTAGGTGTAGAATACTGAGGTTTACGTGAAAGTATGTTTAGTCGTTACTC

541    AGAGAATATGTTGAGGCAGGGATACAGAATTGTTGGAATGATTGGTGATCAATGGAGCGA  600
       TCTCTTATACAACTCCGTCCCTATGTCTTAACAACCTTACTAACCACTAGTTACCTCGCT

601    TCTGCTTGGAGACCACATGGGCGAATCTAGAACCTTTAAGCTTCCTAATCCCATGTACTA  660
       AGACGAACCTCTGGTGTACCCGCTTAGATCTTGGAAATTCGAAGGATTAGGGTACATGAT

661    CATGGAGGCGGCCGC   675
       GTACCTCCGCCGGCG
                   NotI
```

Fig. 4

SEQUENCE LISTING

<160> NUMBER OF SEQ ID NOS: 11

<210> SEQ ID NO 1
<211> LENGTH: 218
<212> TYPE: PRT
<213> ORGANISM: Glycine max

<400> SEQUENCE: 1

Arg Ser Ser Glu Val Lys Cys Ala Ser Phe Arg Leu Ala Val Glu Ala
 1               5                  10                  15

His Asn Ile Arg Ala Phe Lys Thr Ile Pro Glu Glu Cys Val Ser Pro
                20                  25                  30

Thr Lys Asp Tyr Ile Asn Gly Glu Gln Phe Arg Ser Asp Ser Lys Thr
            35                  40                  45

Val Asn Gln Gln Ala Phe Phe Tyr Ala Ser Glu Arg Glu Val His His
        50                  55                  60

-continued

```
Asn Asp Ile Phe Ile Phe Gly Ile Asp Asn Thr Val Leu Ser Asn Ile
 65                  70                  75                  80

Pro Tyr Tyr Glu Lys His Gly Tyr Gly Val Glu Phe Asn Glu Thr
             85                  90                  95

Leu Tyr Asp Glu Trp Val Asn Lys Gly Asp Ala Pro Ala Leu Pro Glu
            100                 105                 110

Thr Leu Lys Asn Tyr Asn Lys Leu Leu Ser Leu Gly Phe Lys Ile Val
            115                 120                 125

Phe Leu Ser Gly Arg Tyr Leu Asp Lys Met Ala Val Thr Glu Ala Asn
130                 135                 140

Leu Lys Lys Ala Gly Phe His Thr Trp Glu Gln Leu Ile Leu Lys Asp
145                 150                 155                 160

Pro His Leu Ile Thr Pro Asn Ala Leu Ser Tyr Lys Ser Ala Met Arg
            165                 170                 175

Glu Asn Leu Leu Arg Gln Gly Tyr Arg Ile Val Gly Ile Ile Gly Asp
            180                 185                 190

Gln Trp Ser Asp Leu Leu Gly Asp His Arg Gly Glu Ser Arg Thr Phe
            195                 200                 205

Lys Leu Pro Asn Pro Met Tyr Tyr Ile Glu
210                 215

<210> SEQ ID NO 2
<211> LENGTH: 218
<212> TYPE: PRT
<213> ORGANISM: Glycine max

<400> SEQUENCE: 2

Arg Thr Pro Glu Val Lys Cys Ala Ser Trp Arg Leu Ala Val Glu Ala
  1               5                  10                  15

His Asn Ile Phe Gly Phe Glu Thr Ile Pro Glu Glu Cys Val Glu Ala
             20                  25                  30

Thr Lys Glu Tyr Ile His Gly Glu Gln Tyr Arg Ser Asp Ser Lys Thr
         35                  40                  45

Val Asn Gln Gln Ala Tyr Phe Tyr Ala Arg Asp Leu Glu Val His Pro
 50                  55                  60

Lys Asp Thr Phe Val Phe Ser Ile Asp Asn Thr Val Leu Ser Asn Ile
 65                  70                  75                  80

Pro Tyr Tyr Lys Lys His Gly Tyr Gly Val Glu Lys Phe Asn Ser Thr
             85                  90                  95

Leu Tyr Asp Glu Trp Val Asn Lys Gly Asn Ala Pro Ser Leu Pro Glu
            100                 105                 110

Thr Leu Lys Asn Tyr Asn Lys Leu Val Ser Leu Gly Phe Lys Ile Ile
            115                 120                 125

Phe Leu Ser Gly Arg Thr Leu Asp Lys Gln Ala Val Thr Glu Ala Asn
130                 135                 140

Leu Lys Lys Ala Gly Tyr His Thr Trp Glu Lys Leu Ile Leu Lys Asp
145                 150                 155                 160

Pro Gln Pro Ser Thr Pro Asn Ala Val Ser Tyr Lys Thr Ala Ala Arg
            165                 170                 175

Glu Lys Leu Ile Arg Gln Gly Tyr Asn Ile Val Gly Ile Ile Gly Asp
            180                 185                 190

Gln Trp Ser Asp Leu Leu Gly Gly His Arg Gly Glu Ser Arg Thr Phe
            195                 200                 205

Lys Leu Pro Asn Pro Leu Tyr Tyr Ile Gln
210                 215
```

```
<210> SEQ ID NO 3
<211> LENGTH: 214
<212> TYPE: PRT
<213> ORGANISM: Lycopersicon esculentum

<400> SEQUENCE: 3

Leu Lys Cys Thr Thr Trp Arg Phe Val Val Glu Thr Asn Asn Leu Ser
 1               5                  10                  15

Pro Trp Lys Thr Ile Pro Glu Glu Cys Ala Asp Tyr Val Lys Glu Tyr
            20                  25                  30

Met Val Gly Pro Gly Tyr Lys Met Glu Ile Asp Arg Val Ser Asp Glu
        35                  40                  45

Ala Gly Glu Tyr Ala Lys Ser Val Asp Leu Gly Asp Gly Arg Asp
    50                  55                  60

Val Trp Ile Phe Asp Val Asp Glu Thr Leu Leu Ser Asn Leu Pro Tyr
 65                  70                  75                  80

Tyr Ser Asp His Arg Tyr Gly Leu Glu Val Phe Asp Asp Val Glu Phe
                85                  90                  95

Asp Lys Trp Val Glu Asn Gly Thr Ala Pro Ala Leu Gly Ser Ser Leu
            100                 105                 110

Lys Leu Tyr Gln Glu Val Leu Lys Leu Gly Phe Lys Val Phe Leu Leu
        115                 120                 125

Thr Gly Arg Ser Glu Arg His Arg Ser Val Thr Val Glu Asn Leu Met
    130                 135                 140

Asn Ala Gly Phe His Asp Trp His Lys Leu Ile Leu Arg Gly Ser Asp
145                 150                 155                 160

His Gly Lys Thr Ala Thr Thr Tyr Lys Ser Glu Arg Arg Asn Ala Met
                165                 170                 175

Val Glu Glu Gly Phe Arg Ile Val Gly Asn Ser Gly Asp Gln Trp Ser
            180                 185                 190

Asp Leu Leu Gly Ser Ser Met Ser Tyr Arg Ser Phe Lys Leu Pro Asn
        195                 200                 205

Pro Met Tyr Tyr Ile Leu
    210

<210> SEQ ID NO 4
<211> LENGTH: 217
<212> TYPE: PRT
<213> ORGANISM: Phaseolus vulgaris

<400> SEQUENCE: 4

Ser Asp Thr Glu Val Arg Cys Ala Ser Trp Arg Leu Ala Val Glu Ala
 1               5                  10                  15

Gln Asn Ile Phe Gly Phe Glu Thr Ile Pro Gln Gln Cys Val Asp Ala
            20                  25                  30

Thr Ala Asn Tyr Ile Glu Gly Gly Gln Tyr Arg Ser Asp Ser Lys Thr
        35                  40                  45

Val Asn Gln Gln Ile Tyr Phe Phe Ala Arg Asp Arg His Val His Glu
    50                  55                  60

Asn Asp Val Ile Leu Phe Asn Ile Asp Gly Thr Ala Leu Ser Asn Ile
 65                  70                  75                  80

Pro Tyr Tyr Ser Gln His Gly Tyr Gly Ser Glu Lys Phe Asp Ser Glu
                85                  90                  95

Arg Tyr Asp Glu Glu Phe Val Asn Lys Gly Glu Ala Pro Ala Leu Pro
            100                 105                 110
```

```
Glu Thr Leu Lys Asn Tyr Asn Lys Leu Val Ser Leu Gly Tyr Lys Ile
            115                 120                 125

Ile Phe Leu Ser Gly Arg Leu Lys Asp Lys Arg Ala Val Thr Glu Ala
        130                 135                 140

Asn Leu Lys Lys Ala Gly Tyr Asn Thr Trp Glu Lys Leu Ile Leu Lys
145                 150                 155                 160

Asp Pro Ser Asn Ser Ala Glu Asn Val Val Tyr Lys Thr Ala Glu Arg
                165                 170                 175

Ala Lys Leu Val Gln Glu Gly Tyr Arg Ile Val Gly Asn Ile Gly Asp
            180                 185                 190

Gln Trp Asn Asp Leu Lys Gly Glu Asn Arg Ala Ile Arg Ser Phe Lys
        195                 200                 205

Leu Pro Asn Pro Met Tyr Tyr Thr Lys
    210                 215
```

<210> SEQ ID NO 5
<211> LENGTH: 214
<212> TYPE: PRT
<213> ORGANISM: Arabidopsis thaliana

<400> SEQUENCE: 5

```
Pro Asn Cys Arg Ser Trp His Leu Gly Phe Glu Thr Ser Asn Met Ile
  1               5                  10                  15

Asn Phe Asp Thr Val Pro Ala Asn Cys Lys Ala Tyr Val Glu Asp Tyr
             20                  25                  30

Leu Ile Thr Ser Lys Gln Tyr Gln Tyr Asp Ser Lys Thr Val Asn Lys
         35                  40                  45

Glu Ala Tyr Phe Tyr Ala Lys Gly Leu Ala Leu Lys Asn Asp Thr Ile
     50                  55                  60

Asn Val Trp Ile Phe Asp Leu Asp Asp Thr Leu Leu Ser Ser Ile Pro
 65                  70                  75                  80

Tyr Tyr Ala Lys Tyr Gly Tyr Gly Thr Glu Asn Thr Ala Ala Gly Ala
                 85                  90                  95

Tyr Trp Ser Trp Leu Val Ser Gly Glu Thr Pro Gly Leu Pro Glu Thr
            100                 105                 110

Leu His Leu Tyr Glu Asn Leu Leu Glu Leu Gly Ile Glu Pro Ile Ile
        115                 120                 125

Ile Ser Asp Arg Trp Lys Lys Leu Ser Glu Ile Thr Ile Glu Asn Leu
    130                 135                 140

Lys Ala Val Gly Val Thr Lys Trp Lys His Val Ile Leu Lys Pro Asn
145                 150                 155                 160

Gly Lys Leu Thr Gln Val Val Tyr Lys Ser Lys Val Arg Asn Gly Leu
                165                 170                 175

Val Arg Gln Gly Tyr Asn Ile Val Gly Ile Ile Gly Asp Gln Trp Ala
            180                 185                 190

Asp Leu Val Glu Asp Thr Pro Gly Arg Val Phe Lys Leu Pro Asn Pro
        195                 200                 205

Leu Tyr Tyr Val Pro Ser
    210
```

<210> SEQ ID NO 6
<211> LENGTH: 220
<212> TYPE: PRT
<213> ORGANISM: Arabidopsis thaliana

```
<400> SEQUENCE: 6

Ser Ile Asn Tyr Pro Asn Cys Arg Ser Trp His Leu Gly Val Glu Thr
  1               5                  10                  15

Ser Asn Ile Ile Asn Phe Asp Thr Val Pro Ala Asn Cys Lys Ala Tyr
             20                  25                  30

Val Glu Asp Tyr Leu Ile Thr Ser Lys Gln Tyr Gln Tyr Asp Ser Lys
         35                  40                  45

Thr Val Asn Lys Glu Ala Tyr Phe Tyr Ala Lys Gly Leu Ala Leu Lys
     50                  55                  60

Asn Asp Thr Val Asn Val Trp Ile Phe Asp Leu Asp Asp Thr Leu Leu
 65                  70                  75                  80

Ser Ser Ile Pro Tyr Tyr Ala Lys Tyr Gly Tyr Gly Thr Glu Asn Thr
             85                  90                  95

Ala Pro Gly Ala Tyr Trp Ser Trp Leu Glu Ser Gly Glu Ser Thr Pro
            100                 105                 110

Gly Leu Pro Glu Thr Leu Tyr Leu Tyr Glu Asn Leu Leu Glu Leu Gly
            115                 120                 125

Ile Glu Pro Ile Ile Ser Asp Arg Trp Lys Lys Leu Ser Glu Val
            130                 135                 140

Thr Val Glu Asn Leu Lys Ala Val Gly Val Thr Lys Trp Lys His Leu
145                 150                 155                 160

Ile Leu Lys Pro Asn Gly Ser Lys Leu Thr Gln Val Val Tyr Lys Ser
                165                 170                 175

Lys Val Arg Asn Ser Leu Val Lys Lys Gly Tyr Asn Ile Val Gly Asn
            180                 185                 190

Ile Gly Asp Gln Trp Ala Asp Leu Val Glu Asp Thr Pro Gly Arg Val
            195                 200                 205

Phe Lys Leu Pro Asn Pro Leu Tyr Tyr Val Pro Ser
            210                 215                 220

<210> SEQ ID NO 7
<211> LENGTH: 219
<212> TYPE: PRT
<213> ORGANISM: Arabidopsis thaliana

<400> SEQUENCE: 7

Ser Ile Asn Tyr Ala Asn Cys Arg Ser Trp His Leu Gly Val Glu Thr
  1               5                  10                  15

Ser Asn Ile Ile Asp Phe Asp Thr Val Pro Ala Asn Cys Lys Asp Tyr
             20                  25                  30

Val Glu Asp Tyr Leu Ile Thr Ser Lys Gln Tyr Gln Tyr Asp Ser Lys
         35                  40                  45

Thr Val Cys Lys Glu Ala Tyr Phe Tyr Ala Lys Gly Leu Ala Leu Lys
     50                  55                  60

Asn Asp Thr Val Asn Val Trp Ile Phe Asp Leu Asp Asp Thr Leu Leu
 65                  70                  75                  80

Ser Ser Ile Pro Tyr Tyr Ala Lys Tyr Gly Tyr Gly Thr Glu Lys Thr
             85                  90                  95

Asp Pro Gly Ala Tyr Trp Leu Trp Leu Gly Thr Gly Ala Ser Thr Pro
            100                 105                 110

Gly Leu Pro Glu Gly Leu Tyr Leu Tyr Gln Asn Ile Ile Glu Val Gly
            115                 120                 125

Ile Glu Pro Ile Ile Leu Ser Val Arg Trp Lys Leu Trp Lys Asn Val
            130                 135                 140
```

```
Thr Leu Asn Leu Glu Ala Ala Gly Val Thr Tyr Trp Lys His Leu Ile
145                 150                 155                 160

Leu Lys Pro Asn Gly Ser Asn Leu Arg Gln Val Val Tyr Lys Ser Lys
                165                 170                 175

Val Arg Asn Lys Leu Val Lys Lys Gly Tyr Asn Ile Val Gly Asn Ile
            180                 185                 190

Gly Asp Gln Trp Ala Asp Leu Val Glu Asp Thr Pro Gly Arg Val Phe
        195                 200                 205

Lys Leu Pro Asn Pro Leu Tyr Tyr Val Pro Ser
    210                 215
```

<210> SEQ ID NO 8
<211> LENGTH: 218
<212> TYPE: PRT
<213> ORGANISM: Glycine max

<400> SEQUENCE: 8

```
Arg Ser Ser Glu Met Lys Cys Ala Ser Phe Arg Leu Ala Val Glu Ala
1               5                   10                  15

His Asn Met Arg Ala Phe Lys Thr Ile Pro Glu Glu Cys Met Glu Pro
            20                  25                  30

Thr Lys Asp Tyr Met Asn Gly Glu Gln Phe Arg Met Asp Ser Lys Thr
        35                  40                  45

Val Asn Gln Gln Ala Phe Phe Tyr Ala Ser Glu Met Glu Met His His
    50                  55                  60

Asn Asp Met Phe Ile Phe Gly Met Asp Asn Thr Met Leu Ser Asn Ile
65                  70                  75                  80

Pro Tyr Tyr Glu Lys His Gly Tyr Gly Val Glu Glu Phe Asn Glu Thr
                85                  90                  95

Leu Tyr Asp Glu Trp Val Asn Lys Gly Asp Ala Pro Ala Leu Pro Glu
            100                 105                 110

Thr Leu Lys Asn Tyr Asn Lys Leu Met Ser Leu Gly Phe Lys Met Val
        115                 120                 125

Phe Leu Ser Gly Arg Tyr Leu Asp Lys Met Ala Val Thr Glu Ala Asn
130                 135                 140

Leu Met Lys Ala Gly Phe His Thr Trp Glu Gln Leu Ile Leu Lys Asp
145                 150                 155                 160

Pro His Leu Met Thr Pro Asn Ala Leu Ser Tyr Lys Ser Ala Met Arg
                165                 170                 175

Glu Asn Met Leu Arg Gln Gly Tyr Arg Ile Val Gly Met Ile Gly Asp
            180                 185                 190

Gln Trp Ser Asp Leu Leu Gly Asp His Met Gly Glu Ser Arg Thr Phe
        195                 200                 205

Lys Leu Pro Asn Pro Met Tyr Tyr Met Glu
    210                 215
```

<210> SEQ ID NO 9
<211> LENGTH: 218
<212> TYPE: PRT
<213> ORGANISM: Glycine max

<400> SEQUENCE: 9

```
Arg Ser Ser Glu Met Lys Cys Ala Ser Phe Arg Leu Ala Val Glu Ala
1               5                   10                  15

His Asn Met Arg Ala Phe Lys Thr Ile Pro Glu Glu Cys Met Glu Met
            20                  25                  30
```

```
Thr Lys Asp Tyr Met Asn Gly Glu Gln Phe Arg Met Asp Ser Lys Thr
        35                  40                  45

Val Asn Gln Gln Ala Phe Phe Tyr Ala Ser Glu Met Glu Met His His
     50                  55                  60

Met Asp Met Phe Ile Phe Gly Met Asp Asn Thr Met Leu Ser Asn Ile
 65                  70                  75                  80

Pro Tyr Tyr Glu Lys His Gly Tyr Gly Met Glu Glu Phe Asn Glu Thr
                 85                  90                  95

Met Tyr Asp Glu Trp Met Asn Lys Gly Asp Ala Pro Ala Leu Pro Glu
            100                 105                 110

Thr Leu Lys Asn Tyr Asn Lys Leu Met Ser Leu Gly Phe Lys Met Val
        115                 120                 125

Phe Met Ser Gly Arg Tyr Met Asp Lys Met Ala Val Thr Glu Ala Asn
130                 135                 140

Leu Met Lys Ala Gly Met His Thr Trp Glu Gln Leu Ile Leu Lys Asp
145                 150                 155                 160

Pro His Leu Met Thr Pro Asn Ala Met Ser Tyr Lys Ser Ala Met Arg
                165                 170                 175

Glu Asn Met Leu Arg Gln Gly Tyr Arg Ile Val Gly Met Ile Gly Asp
            180                 185                 190

Gln Trp Ser Asp Leu Met Gly Asp His Met Gly Glu Ser Arg Met Phe
        195                 200                 205

Lys Leu Pro Asn Pro Met Tyr Tyr Met Glu
        210                 215

<210> SEQ ID NO 10
<211> LENGTH: 218
<212> TYPE: PRT
<213> ORGANISM: Glycine max

<400> SEQUENCE: 10

Arg Ser Ser Glu Met Lys Cys Ala Ser Phe Arg Leu Ala Val Glu Ala
  1               5                  10                  15

His Asn Met Arg Ala Phe Lys Thr Met Pro Glu Glu Cys Met Glu Met
             20                  25                  30

Thr Lys Asp Tyr Met Asn Gly Glu Gln Phe Arg Met Asp Ser Lys Thr
        35                  40                  45

Val Met Gln Gln Ala Phe Phe Tyr Ala Ser Glu Met Glu Met His His
     50                  55                  60

Met Asp Met Phe Ile Phe Gly Met Asp Asn Thr Met Leu Ser Asn Met
 65                  70                  75                  80

Pro Tyr Tyr Glu Lys His Gly Tyr Gly Met Glu Glu Met Asn Glu Thr
                 85                  90                  95

Met Tyr Asp Glu Trp Met Asn Lys Gly Asp Ala Pro Ala Leu Pro Glu
            100                 105                 110

Thr Leu Lys Asn Tyr Asn Lys Leu Met Ser Leu Gly Phe Lys Met Val
        115                 120                 125

Phe Met Ser Gly Arg Tyr Met Asp Lys Met Ala Val Thr Met Ala Asn
130                 135                 140

Leu Met Lys Ala Gly Met His Thr Trp Glu Gln Leu Ile Leu Lys Met
145                 150                 155                 160

Pro His Met Met Thr Pro Asn Ala Met Ser Tyr Lys Ser Ala Met Arg
                165                 170                 175

Glu Asn Met Leu Arg Gln Gly Tyr Arg Ile Val Gly Met Ile Gly Asp
            180                 185                 190
```

```
Gln Trp Ser Asp Leu Met Gly Asp His Met Gly Glu Ser Arg Met Phe
        195                 200                 205

Lys Leu Pro Asn Pro Met Tyr Tyr Met Glu
    210                 215

<210> SEQ ID NO 11
<211> LENGTH: 675
<212> TYPE: DNA
<213> ORGANISM: Glycine max

<400> SEQUENCE: 11
ggcccagccg gccagatctt cggagatgaa atgcgctagc tttaggcttg ctgtggaagc      60
acacaacatg cgagccttta aaaccattcc tgaagagtgc atggaaccaa caaaggacta     120
catgaatggc gaacaatttc gaatggactc taaaacagtt aaccaacagg ccttcttta     180 tgctagtgaa atggaaatgc atcacaacga catgtttata ttcggcatgg ataacaccat     240
gctctctaat atcccatact atgaaaaaca tggatatggg gtggaggaat ttaatgaaac     300
cttatatgat gaatgggtta acaagggcga cgcaccggca ttgccagaga ctcttaaaaa     360
ttacaacaag ctgatgtccc ttggcttcaa gatggtattc ttgtcaggaa ggtaccttga     420
caaaatggcc gtaacagaag caaacctaat gaaggctggc ttccacacat gggagcagtt     480
aattctcaag gatccacatc ttatgactcc aaatgcactt tcatacaaat cagcaatgag     540
agagaatatg ttgaggcagg gatacagaat tgttggaatg attggtgatc aatggagcga     600
tctgcttgga gaccacatgg gcgaatctag aacctttaag cttcctaatc ccatgtacta     660
catggaggcg gccgc                                                     675
```

COMPOSITIONS AND METHODS FOR ALTERING AMINO ACID CONTENT OF PROTEINS

CROSS-REFERENCE TO RELATED APPLICATIONS

This application is a divisional of U.S. application Ser. No. 08/988,015, filed Dec. 10, 1997, now abandoned which is herein incorporated by reference.

FIELD OF THE INVENTION

The invention relates to a process for the production of proteins having high nutritional properties. The methods find particular use in the production of plants with increased levels of amino acids having high nutritional properties through the modification of plant genes.

BACKGROUND OF THE INVENTION

Autotrophic organisms can make all of their own amino acids. Other cells utilize many preformed amino acids. Humans and other higher animals require a number of essential amino acids in the diet. These essential amino acids are obtained directly or indirectly by eating plants. These essential amino acids include lysine, tryptophan, threonine, methionine, phenylalanine, leucine, valine and isoleucine.

Constructing proteins with higher nutritional value has been a long-sought goal of scientists. Traditionally, agricultural scientists concentrated on breeding plants with high nutritional yield. Typically, these new varieties were richer in carbohydrates but usually poorer in essential proteins than the wild type varieties from which they were derived.

Seed storage proteins represent up to 90% of total seed protein in seeds of many plants. They are used as a source of nutrition for young seedlings in the period immediately following germination. The genes encoding them are strictly regulated, being expressed in a highly tissue specific and stage specific manner. These genes are almost exclusively expressed in developing seed. Different classes of seed storage proteins may be expressed at different stages in the development of the seed. They are typically stored in membrane bound organelles called protein bodies or protein storage vacuoles.

A related group of proteins, the vegetative storage proteins, have similar amino acid compositions and are also stored in specialized vacuoles. These proteins are generally found in leaves instead of seeds. These proteins are degraded upon flowering, and are thought to serve as a nutritive source for developing seeds.

Cereal grains and legume seeds which are key protein sources for the vegetarian diet are generally deficient in essential amino acids such as methionine, lysine, and threonine. Therefore, there is needed means for improving the nutritional quality of these proteins.

SUMMARY OF THE INVENTION

Compositions and methods for altering the amino acid profiles of proteins without introducing conformational changes into the protein are provided. The method involves preparing a binding partner and/or an interacting molecule which binds to the native protein and using such interacting molecule to select for modified proteins retaining the native conformation.

The method finds particular use in altering the nutritional value of proteins. A plant protein having increased methionine levels is provided. The modified protein retains the conformation of the native protein while having significantly higher levels of methionine.

BRIEF DESCRIPTION OF THE DRAWINGS

FIGS. 1A and 1B show homologies between vegetative storage protein (VSP) and other proteins, as follows.

VSP-b (same as VSPβ) and VSP-a (same as VSPα): Staswick, P. E., (1988), Plant Physiol. 87, 250–254. The amino acid sequence of the VSP-b protein is set forth in SEQ ID NO:1, and the amino acid sequence of the VSP-a protein is set forth in SEQ ID NO:2.

T.phos (tomato acid phosphatase): Erion, J. L., Ballo, B., May, L., Bussell, J., Fox, T. W., & Thomas, S. R., SwissProt database accession number P27061. The amino acid sequence of this protein is set forth in SEQ ID NO:3.

Ph.vulg (Phaseolus vulgaris): Zhon, P—Y., Tanaka, T., Yamauchi, D., & Minamikawa, T. (1997), Plant Physiol. 113, 479–485. The amino acid sequence of this protein is set forth in SEQ ID NO:4.

Ar.VSP (*Arabidopsis thaliana*): Yu, D. Y., Quigley, F., & Mache, R., EMBL database accession number X79490. The amino acid sequence of this protein is set forth in SEQ ID NO:5.

Ar.1 A-1, Ar17A-1 (*Arabidopsis thaliana*, floral organs): Utsugi, S., Sakamoto, Ogura, Y., Murata, M., & Motoyoshi, F. (1996) Plant Mol. Biol. 32, 759–765. The amino acid sequence of the "Ar.1A-1" protein is set forth in SEQ ID NO:6, and the amino acid sequence of the "Ar17A-1" protein is set forth in SEQ ID NO:7.

FIG. 2 shows proposed VSPβ methionine-enriched variants. The amino acid sequence of the "VSPβ-Met10" protein is set forth in SEQ ID NO:8, the amino acid sequence of the "VSPβ-Met20" protein is set forth in SEQ ID NO:9, and the amino acid sequence of the "VSPβ-Met30" protein is set forth in SEQ ID NO:10.

Figure 3A:
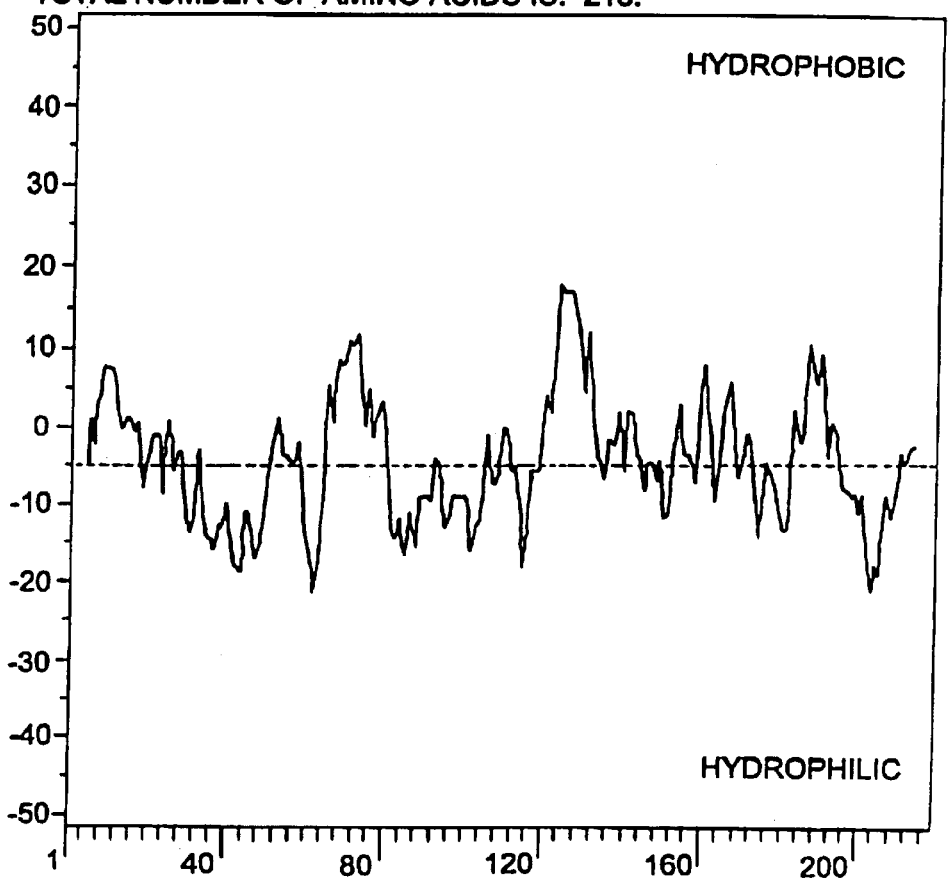

FIG. 3A shows the hydropathy index computation for sequence VSPβ.

Figure 3B:
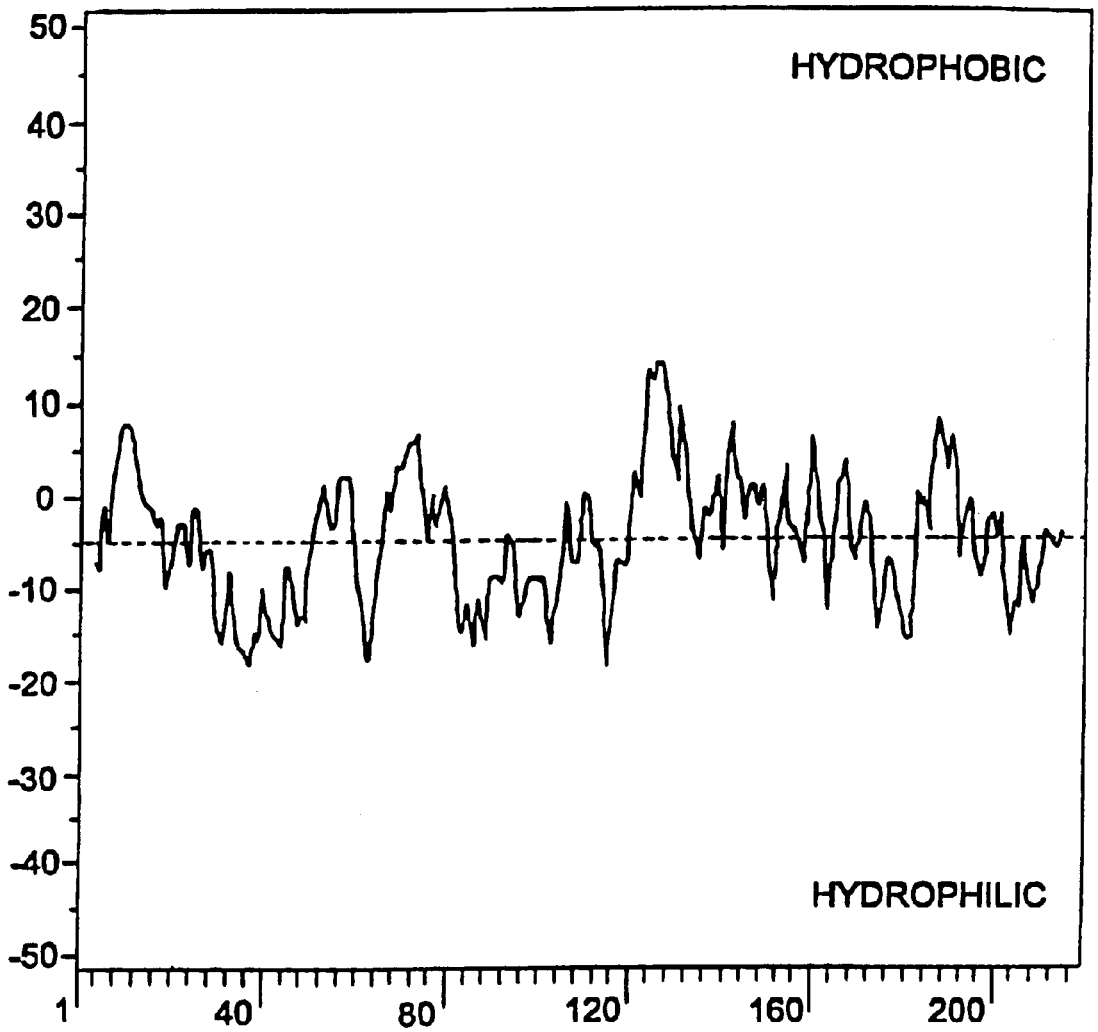

FIG. 3B shows the hydropathy index computation for sequence VSPMet10.

Figure 3C:
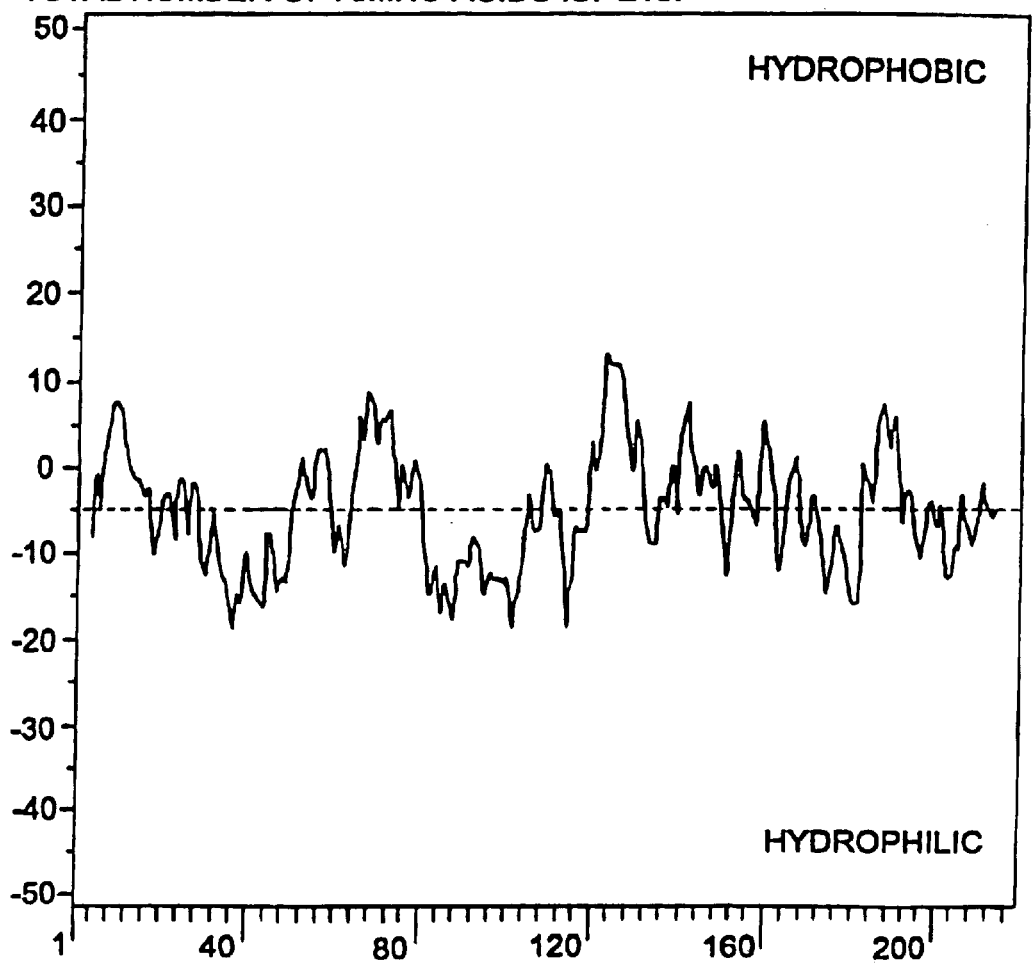

FIG. 3C shows the hydropathy index computation for sequence VSPMet20.

Figure 3D:
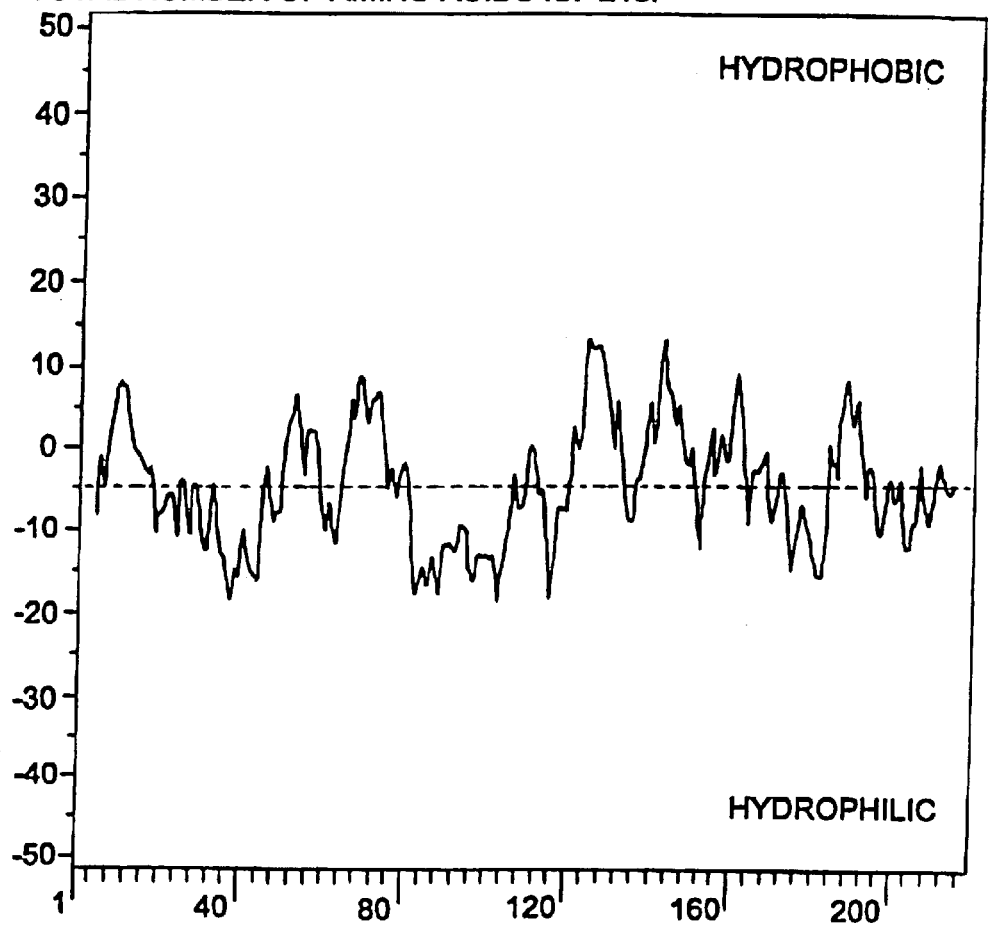

FIG. 3D shows the hydropathy index computation for sequence VSPMet30.

FIG. 4 shows the VSPβ-met10 nucleotide sequence. The VSPβ-met10 nucleotide sequence is also set forth in SEQ ID NO:11.

Figure 5:
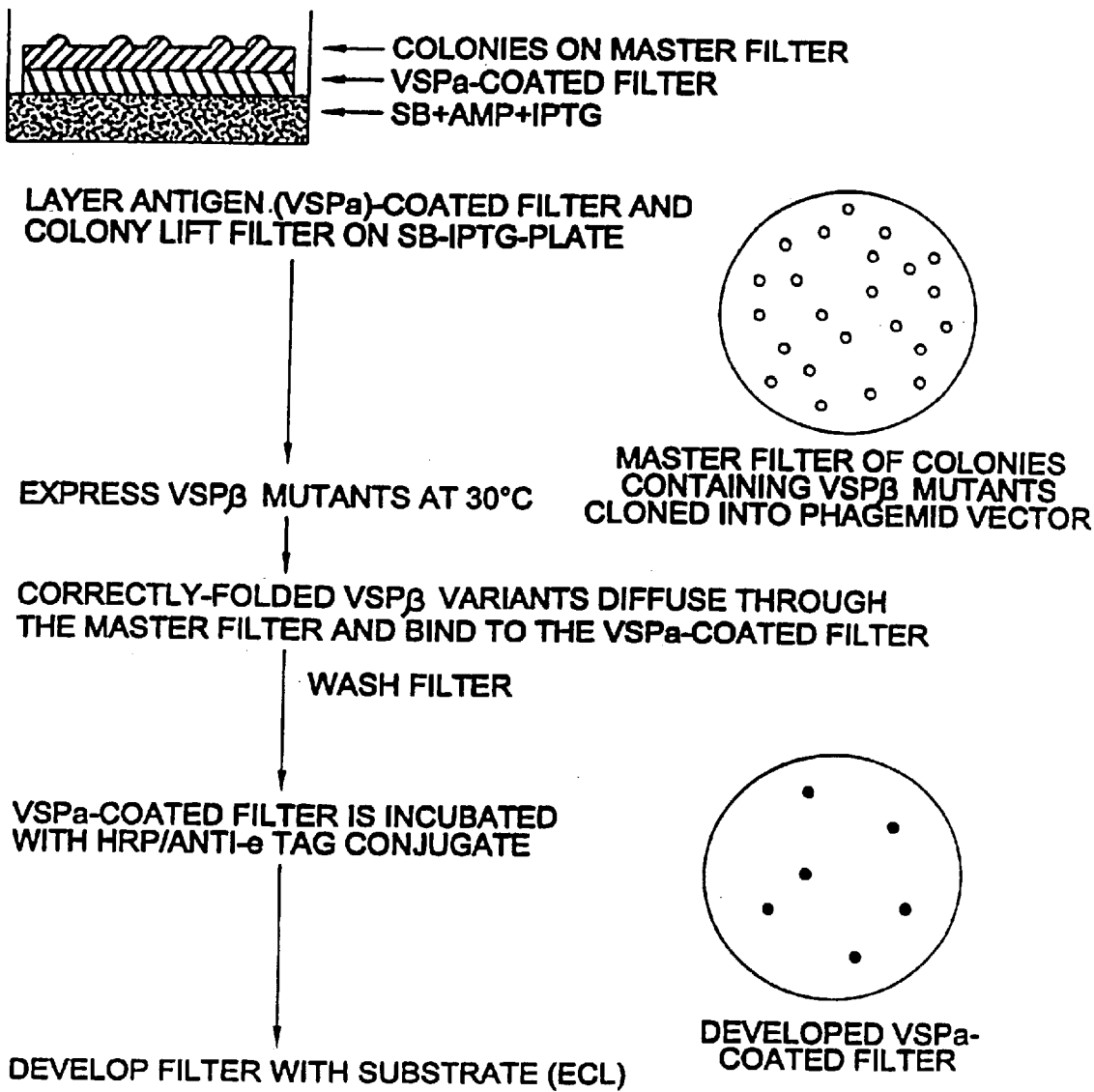

FIG. 5 shows the colony lift assay to detect protein—protein interactions.

DETAILED DESCRIPTION OF THE INVENTION

Proteins having altered amino acid profiles are provided. The proteins can be designed to be enriched in essential amino acids, including lysine, methionine, tryptophan, threonine, phenylalanine, leucine, valine and isoleucine relative to average levels of such amino acids in the native protein.

Generally, knowledge of the three-dimensional (3-D) structure of a given protein allows one to engineer amino acid substitutions in a rational manner so as to effect a desired change in the property of the protein without compromising the folding process. The present invention provides methods for increasing the levels of essential amino acids within a protein while at the same time the altered protein has the conformation of the native protein.

The present invention provides methods for altering the amino acid content of a protein whose 3-D structure is unknown or unavailable. The method may also provide an easy method for assessing changes in a protein in which the structure of the protein is known but tools for confirming conformation of the protein may be unavailable. The "conformation" of a protein refers to the spatial arrangement of substituent groups of the molecule. The polypeptide chain of a protein has only one conformation (or a very few) under normal biological conditions of temperature and pH. This, referred to as the "native conformation," confers biological activity. The native conformation is sufficiently stable so that the protein can be isolated and retained in its native state. Therefore, it is important to be able to change the amino acid content of a protein, yet at the same time have the protein retain its biological activity.

The methods of the invention are useful for making amino acid changes within proteins whose conformation is unknown or unavailable. Such proteins include the vegetative storage protein which is believed to play a significant role in supplying amino acids for protein deposition during seed fill, and other proteins of the seed. The methods of the invention may be used to modify the amino acid composition of any protein. Examples of such proteins include but are not limited to wheat endosperm purothionine (Mak and Jones (1976) Can. J. Biochem. 22:83J); albumins (Higgins et al. (1986) J. Biol. Chem. 261:11124); and methionine rich proteins (Pedersen et al. (1986) J. Biol. Chem. 261:6279; Kirihara et al. (1988) Gene 71:359; Musumura et al. (1989) Plant. Mol. Biol. 12:123).

The methods of the invention comprise altering the amino acid composition of a protein to produce an engineered protein. The engineered protein will retain the conformation and activity of the native protein yet have a modified or altered amino acid content. In this manner, levels of particular amino acids of interest can be increased or decreased. Of particular interest, is to increase the levels or numbers of essential amino acids in the proteins. By essential amino acid is intended, lysine, tryptophan, threonine, methionine, phenylalanine, leucine, valine, isoleucine, and cysteine. However, it is recognized that the amino acid composition can be changed in various ways, as long as the changes do not affect the conformation of the final protein.

The proteins of the invention have been engineered or modified to contain altered amino acid levels. The engineered protein retains the conformation of the native protein. The method involves preparing binding partners and/or interacting molecules to the native protein and utilizing these interacting molecules to determine whether the engineered protein folds correctly. By "binding partner" or "interacting molecule" is intended a molecule which is capable of binding or interacting with the proteins of interest. Such binding partners or interacting molecules include antibodies, monoclonal antibodies, antibody fragments, proteins, modified proteins, nucleotide sequences, such as aptomers, chemical compounds (e.g. carbohydrates, etc.), or combinations thereof. The interacting molecules also encompass polypeptides that have an intrinsic affinity to the protein of interest, particularly such polypeptides that are capable of binding with the protein of interest to form an oligomeric complex. For example, VSP-alpha binds VSP with high affinity and could be used as an interacting molecule for the altered VSP protein.

Methods for antibody production are known in the art. See, for example, Antibodies, A Laboratory Manual, Harlow and Lane (Eds.), Cold spring Harbor Laboratory Press, Coldspring Harbor, N.Y. (1988), and the references cited therein. See also, Radka et al. (1983) J. Immunol. 128:2804; and Radka et al. (1984) Immunogenetics 19:63. All of which are herein incorporated by reference.

Once antibodies, preferably monoclonal antibodies, are available which bind to the native protein, such antibodies can be used to select for modified proteins which retain the conformation of the native protein. Strategies to identify residues within a protein that might tolerate amino acid substitution include mutational analysis, secondary structure prediction, homology comparison, and the like. Such strategies can be used to identify amino acids within the protein that will tolerate amino acid substitution. By mutational analysis is intended mutagenic PCR and DNA shuffling. See, for example, Stemmer, W. P. (1994) Nature 370:389–391; and Stemmer, W. P. (1994) Proc. Natl. Acad. Sci. USA 91:10747–10751, herein incorporated by reference. Such methods can be used to generate phage display libraries of protein genes containing random mutations. Phage display is an in vitro selection technology which allows for a foreign protein or peptide to be displayed on the surface of filamentous phage, linking the phenotype of the phage to its genotype. Molecular repertoires with sufficient diversity can be generated using such technology. Proteins which exhibit the correct conformation, that is, the native conformation, can be selected for by the ability to bind antibodies recognizing conformational domains of the native protein. See also Methods in Enzymology, Combinatorial Chemistry, John N. Abelson (Ed.), Vol. 267, Academic Press, Inc., San Diego, Calif., herein incorporated by reference. Once correctly-folded protein variants are determined, subsequent isolation and sequencing of the variants reveals the tolerated sites for mutations. Alternatively, correctly folded variants may be identified by other screening or selection methods such as filter lift-assay and ELISA.

Substitutions may also be incorporated at secondary structure prediction sites. Structural features of the protein are important for proper folding. Sequence analysis tools such as the GCG (Wisconsin sequence analysis package, Genetics Computer Group, University Research Park, 575 Science Drive, Madison, Wis.) and PC/GENE (Oxford Molecular Group, 2105 S. Bascom Avenue, Suite 200, Campbell, Calif.) can be used to analyze protein sequence for secondary structure features such as helices, sheets and turns. In this manner, it can be determined whether a particular stretch of amino acids may reside on the surface of the protein. Residues on the surface of a protein tolerate substitution more readily than buried residues without compromising the structure of the protein. Utilizing these algorithms, predicted turns and surface regions of the proteins can be made. Therefore, predictions can be made into which regions amino acid substitutions can be made without affecting conformation.

Sites for amino acid substitution can also be determined by homology comparison to other proteins. Nature has tested the tolerance of protein residues to substitution as exemplified in the sequences of proteins such as globins and cytochromes from several different species, members of which have the same fold. See, for example, Hampsey et al. (1988) FEBS Lett. 231:275; Bashford et al. (1987) J. Mol. Biol. 196:199; Lesk and Chothia (1980) J. Mol. Biol. 136:225.

In designing proteins of the invention, hydrophobic residues, such as alanine, cysteine, valine, isoleucine, leucine, methionine, phenylalanine, and tryptophan may be substituted for one another without undue perturbation of the structure. Such residues generally occur in the hydrophobic core of the protein. See, Bowie et al. (1990) Science 247:1306–1310; and Baldwin and Matthews (1994) Curr. Opin. Biotech 5:396–402. See also Ladunga and Smith (1997) Prot. Eng. 10:187–196, herein incorporated by reference. Generally, residues that substitute for one another in related sequences do so by conserving the physico-chemical properties of the residue and folding of the protein thus conserving the 3-D structure of the protein.

Therefore, the protein to be modified can be compared with homologous proteins. Amino acids that are critical to the function and/or folding of the protein would be expected to be conserved over time. Therefore, predictions can be made as to which amino acids can be substituted without affecting the conformation or folding of the protein.

Such selected amino acid substitutions can be made by DNA sequencing, site-directed mutagenesis, or other methods which substitute one amino acid with any other amino acid.

Once the amino acid substitutions have been made and the conformation confirmed by antibody binding, the protein can be expressed using known expression systems. Where necessary, the DNA encoding the protein can be synthesized using known techniques. Likewise, the nucleotide sequence encoding the protein can be contained within expression cassettes.

Utilizing the methods of the invention, proteins can be constructed which have increased nutritional quality. That is, the essential amino acid content within the protein can be increased to represent at least about 5-about 10%, preferably at least about 10-about 20%, more preferably at least about 20-about 40% of the total amino acid content in the protein.

In the same manner, the amino acid content of a subject protein can be altered to include at least about 10% amino acid substitutions, additions or deletions, about 20% or even up to about 30% to about 40%. It is recognized that the limitation will be the activity of the altered. The present invention provides a convenient and ready mechanism to test the activity of the protein by its ability to bind the interacting molecule.

For convenience for expression in plants, the nucleic acid encoding the modified peptides or proteins of the invention can be contained within expression cassettes. The expression cassette will comprise a transcriptional initiation region linked to the nucleic acid encoding the peptide of interest. Such an expression cassette is provided with a plurality of restriction sites for insertion of the gene or genes of interest to be under the transcriptional regulation of the regulatory regions.

The transcriptional initiation region, the promoter, may be native or homologous or foreign or heterologous to the host, or could be the natural sequence or a synthetic sequence. By foreign is intended that the transcriptional initiation region is not found in the wild-type host into which the transcriptional initiation region is introduced.

The transcriptional cassette will include the in 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens*, such as the octopine synthase and nopaline synthase termination regions. See also, Guerineau et al., (1991) Mol. Gen. Genet. 262:141–144; Proudfoot (1991) Cell 64:671–674; Sanfacon et al. (1991) Genes Dev. 5:141–149; Mogen et al. (1990) Plant Cell 2:1261–1272; Munroe et al. (1990) Gene 91:151–158; Ballas et al. 1989) Nucleic Acids Res. 17:7891–7903; Joshi et al. (1987) Nucleic Acid Res. 15:9627–9639.

Where appropriate, the gene(s) expressing the modified proteins may be optimized for increased expression in the transformed plant. In this manner, the sequences can be synthesized using monocot, dicot or particular plant; i.e. maize, soybean, sorghum, wheat, etc., preferred codons for improved expression. Methods are available in the art for synthesizing plant preferred genes. See, for example, U.S. Pat. Nos. 5,380,831, 5,436, 391, and Murray et al. (1989) Nucleic Acids Res. 17:477–498, herein incorporated by reference.

The expression cassettes may additionally contain 5' leader sequences in the expression cassette construct. Such leader sequences can act to enhance translation. Translation leaders are known in the art and include: picomavirus leaders, for example, EMCV leader (Encephalomyocarditis 5' noncoding region) (Elroy-Stein, O., Fuerst, T. R., and Moss, B. (1989) PNAS USA, 86:6126–6130); potyvirus leaders, for example, TEV leader (Tobacco Etch Virus) (Allison et al. (1986); MDMV leader (Maize Dwarf Mosaic Virus); Virology, 154:9–20), and human immunoglobulin heavy-chain binding protein (BiP), (Macejak, D. G., and P. Sarnow (1991) Nature, 353:90–94; untranslated leader from the coat protein mRNA of alfalfa mosaic virus (AMV RNA 4), (Jobling, S. A., and Gehrke, L., (1987) Nature, 325:622–625; tobacco mosaic virus leader (TMV), (Gallie, D. R. et al. (1989) Molecular Biology of RNA, pages 237–256; and maize chlorotic mottle virus leader (MCMV) (Lommel, S. A. et al. (1991) Virology, 81:382–385). See also, Della-Cioppa et al. (1987) Plant Physiology, 84:965–968. Other methods known to enhance translation can also be utilized, for example, introns, and the like.

The expression cassettes may contain one or more than one nucleic acid sequences to be transferred and expressed in the transformed plant. Thus, each nucleic acid sequence will be operably linked to 5' and 3' regulatory sequences. Alternatively, multiple expression cassettes may be provided.

Generally, the expression cassette will comprise a selectable marker gene for the selection of transformed cells. Selectable marker genes are utilized for the selection of transformed cells or tissues. Such selectable marker genes are known in the art. See generally, G. T. Yarranton (1992) Curr. Opin. Biotech., 3:506–511; Christopherson et al. (1992) Proc. Natl. Acad. Sci. USA, 89:6314–6318; Yao et al. (1992) Cell, 71:63–72, W. S. Reznikoff (1992) Mol. Microbiol., 6:2419–2422; Barkley et al. (1980) The Operon, pp. 177–220; Hu et al. (1987) Cell, 48:555–566; Brown et al. (1987) Cell, 49:603–612; Figge et al. (1988) Cell, 52:713–722; Deuschle et al. (1989) Proc. Natl. Acad. Aci. USA, 86:5400–5404; Fuerst et al. (1989) Proc. Natl. Acad. Sci. USA, 86:2549–2553; Deuschle et al. (1990) Science, 248:480–483; M. Gossen (1993) PhD Thesis, University of Heidelberg; Reines et al. (1993) Proc. Natl. Acad. Sci. USA, 90:1917–1921; Labow et al. (1990) Mol. Cell Bio., 10:3343–3356; Zambretti et al. (1992) Proc. Natl. Acad. Sci. USA, 89:3952–3956; Baim et al. (1991) Proc. Natl. Acad. Sci. USA, 88:5072–5076; Wyborski et al. (1991) Nuc. Acids Res., 19:4647–4653; A. Hillenand-Wissman (1989) Topics in Mol. and Struc. Biol., 10:143–162; Degenkolb et al. (1991) Antimicrob. Agents Chemother., 35:1591–1595; Kleinschnidt et al. (1988) Biochemistry, 27:1094–1104;

Gatz et al. (1992) Plant J., 2:397–404; A. L. Bonin (1993) PhD Thesis, University of Heidelberg; Gossen et al. (1992) Proc. Natl. Acad. Sci. USA, 89:5547–5551; Oliva et al. (1992) Antimicrob. Agents Chemother., 36:913–919; Hlavka et al. (1985) Handbook of Exp. Pharmacology, 78; Gill et al. (1988) Nature 334:721–724; DeBlock et al. (1987) EMBO J., 6:2513–2518; DeBlock et al. (1989) Plant Physiol., 91:691–704; Fromm et al. (1990) 8:833–839; Gordon-Kamm et al. (1990) 2:603–618. Such disclosures are herein incorporated by reference.

The nucleotide sequences of interest of this invention can be introduced into the genome of the desired host organism in a variety of techniques known in the art. For the purposes of this invention, it will be appreciated to those skilled in the art that any conventional transformation vector may be used as long as it is capable of transforming the organism of choice and it does not have restriction sites in common with those comprising the final master insertion cassette. Hence, the detailed experimental description of transformation vectors is given by way of illustration only.

Vector systems are known for the transformation of yeast and bacterial cells. For yeast, these include but are not limited to autonomously replicating plasmids (see, for example, Stearns et al. (1990) Methods Enzymol. 185:280–297); 2-micron circle yeast DNA sequences (see, for example, Hollenberg (1982) Curr. Topics Microbiol. Immunol. 96:119–144; Broach (1983) Methods Enzymol. 101:307–325; MacKay (1983) Methods Enzymol. 101:325–343, Armstrong (1989) BioTechnology 13:165–192, Rose (1990) Methods Enzymol. 185:234–279); linearized vector DNA (see, for example, see, for example, Takita et al. (1997) Yeast 13:763–768); artificial chromosome vectors (Burke (1987) Science 236:806–812); restriction site bank plasmids (Davison (1987), U.S. Pat. No. 4,657,858, and Methods Enzymol. 153:34–54); delta-integration vectors (see, for example, Lee and Da Silva (1997) Biotechnol. Prog. 13:368–373); and *Agrobacterium*-based vectors (see, for example, Bundock et al. (1995) EMBO J. 14:3206–3214; Piers et al. (1996) Proc. Natl. Acad. Sci. USA 93:1613–1618; Risseeuw et al. (1996) Mol. Cell. Biol. 16:5924–5932); and Shuttle Vectors (see, for example, Schneider (1991) Methods Enzymol 194:373–388; Singh (1997) Methods Mol. Biol. 62:113–130). See generally Hinnen (1980) Curr. Topics Microbiol. Immunol. 96:101–117; Nombela (1985) Revis. Biol. Cel. 4:1–25; Parent (1985) Yeast 1(2):83–138; West (1988) BioTechnology 10:387–404; Schena (1991) Methods Enzymol. 194:389–398; Schneider (1991) Methods Enzymol. 194:373–388; and Singh (1997) Methods. Mol. Biol. 62:113–130.

Vector systems used for bacterial transformation include, but are not limited to, yeast shuttle vectors (see, for example, Ward (1990) Nucleic Acids Res. 18(17):5319; Strathern (1991) Methods Enzymol. 194:319–329; Soni (1992) Nucleic Acids Res. 20(21) 5852; Nacken (1994) Nucleic Acids Re. 22:1509–1510; Wehmeier (1995) Gene 165:149–150); pBR322 and related plasmids such as pBR327 and pKC7 (see, for example, Rao and Rogers (1979) Gene 7:79–82, Talmadge and Gilbert (1980) Gene 12:235–241; Smith et al. (1995) Microbiology 141(pt. 1): 181–188); pATH vectors (see, for example, Koerner et al. (1991) Methods in Enzymol. 194:477–490); yeast plasmids (see, for example, Marcil (1992) Nucleic Acids Res. 20:917); and natural replicon ColEI and related plasmids such as P15A, F, RSF1010, and R616 (see, for example, Muhlenhoff and Chauvat (1996) Mol. Gen. Genet. 252:93–100; Sakai and Komano (1996) Biosci. Biotechnol. Biochem. 60:377–382; Lee and Henk (1997) Vet. Microbiol. 54:369–374); herein incorporated by reference.

A number of vector systems are also known for the introduction of foreign or native genes into mammalian cells. These include SV40 virus (see, for example, Okayama et al. (1985) Molec. Cell. Biol. 5:1136–1142); Bovine papilloma virus (see, for example, DiMaio et al. (1982) Proc. Natl. Acad. Sci. USA 79:4030–4034); adenovirus (see, for example, Morin et al. (1987) Proc. Natl. Acad. Sci. USA 84:4626; Yifan et al. (1995) Proc. Natl. Acad. Sci. USA 92:1401–1405; Yang et al. (1996) Gene Ther. 3:137–144; Tripathy et al. (1996) Nat. Med. 2:545–550; Quantin et al. (1992) Proc. Natl. Acad. Sci. USA 89:2581–2584; Rosenfeld et al. (1991) Science 252:431–434, Wagner (1992) Proc. Natl. Acad. Sci. USA 89:6099–6103; Curiel et al. (1992) Human Gene Therapy 3:147–154; Curiel (1991) Proc. Natl. Acad. Sci. USA 88:8850–8854; LeGal LaSalle et al. (1993) Science 259:590–599); Kass-Eisler et al. (1993) Proc. Natl. Acad. Sci. USA 90:11498–11502); adeno-associated virus (see, for example, Muzyczka et al. (1994) J. Clin. Invest. 94:1351; Xiao et al. (1996) J. Virol. 70:8098–8108); herpes simplex virus (see, for example, Geller et al., (1988) Science 241:1667; Huard et al. (1995) Gene Therapy 2:385–392; U.S. Pat. No. 5,501,979); retrovirus-based vectors (see, for example, Curran et al. (1982) J. Virol., 44:674–682; Gazit et al. (1986) J. Virol., 60:19–28; Miller (1992) Curr. Top. Microbiol. Immunol. 158:1–24; Cavanaugh et al. (1994) Proc. Natl. Acad. Sci. USA 91:7071–7075; Smith et al. (1990) Mol. Cell. Biol. 10:3268–3271); herein incorporated by reference.

Methods of the present invention can be used to facilitate assembly of nucleotide sequences of interest for transformation of any plant. In this manner, genetically modified plants, plant cells, plant tissue, seed, and the like can be obtained. The transformation vector and hence method of transformation chosen will depend on the type of plant or plant cell, i.e. monocot or dicot, targeted for transformation. Suitable methods of transforming plant cells include microinjection (Crossway et al. (1986) Biotechniques 4:320–334); electroporation (Riggs et al. (1986) Proc. Natl. Acad. Sci. USA 83:5602–5606); *Agrobacterium*-mediated transformation (Hinchee et al. (1988) Biotechnology 6:915–921); direct gene transfer (Paszkowski et al. (1984) EMBO J. 3:2717–2722); and ballistic particle acceleration (see, for example, Sanford et al. U.S. Pat. No. 4,945,050; WO91/10725 and McCabe et al. (1988) Biotechnology 6:923–926). Also see, Weissinger et al. (1988) Annual Rev. Genet. 22:421–477; Sanford et al. (1987) Particulate Science and Technology 5:27–37 (onion); Christou et al. (1988) Plant Physiol. 87:671–674 (soybean); McCabe et al. (1988) Bio-Technology 6:923–926 (soybean); Datta et al. (1990) Biotechnology 8:736–740 (rice); Klein et al. (1988) Proc. Natl. Acad. Sci. USA 85:4305–4309 (maize); Klein et al. (1988) BioTechnology 6:559–563 (maize); WO91/10725 (maize); Klein et al. (1988) Plant Physiol. 91:440–444 (maize); Fromm et al. (1990) BioTechnology 8:833–839; and Gordon-Kamm et al. (1990) Plant Cell 2:603–618 (maize); Hooydaas-Van Slogteren and Hooykaas (1984) Nature (London) 311:763–764; Bytebier et al. (1987) Proc. Natl. Acad. Sci. USA 84:5345–5349 (Liliaceae); De Wet et al. (1985) In The Experimental Manipulation of Ovule Tissues, ed. G. P. Chapman et al., pp. 197–209 (Longman, N. Y.) (pollen); Kaeppler et al. (1990) Plant Cell Reports 9:415–418; and Kaeppler et al. (1992) Theor. Appl. Genet. 84:560–566 (whisker-mediated transformation); D'Halluin et al. (1992) Plant Cell 4:1495–1505 (electroporation); Li et al. (1993) Plant Cell Reports 12:250–255, and Christou and Ford (1995) Annals of Botany 75:407–413 (rice); Osjoda et al. (1996) BioTechnology 14:745–750 (maize via *Agrobacterium tumefaciens*); all of which are herein incorporated by reference. The following examples are offered by way of illustration and not by way of limitation.

EXPERIMENTAL

Three complementary strategies, namely, mutational analysis, secondary structure prediction, and homology comparison (see below) have been used to identify amino acids within VSPβ (vegetative storage protein) that might tolerate methionine substitution Together, results from these strategies facilitated the design of three VSP variants with increasing methionine content.

1. Mutational Analysis

The simple premise behind this strategy was that if one prepared monoclonal antibodies that recognized the wild-type VSP, then these same antibodies would, if the mutant proteins folded correctly, also recognize the engineered proteins. As a first step, therefore, mice were injected with VSP purified from soybean leaves, and a panel of 21 monoclonal antibodies recognizing wild-type VSP has been characterized by ELISA. These antibodies also recognize VSPα expressed and purified from *Pichia pastoris*. The following two approaches can be implemented to generate either random or "semi-rational" mutations in VSPβ. Mutagenic PCR and DNA shuffling (Stemmer, W. P. (1994) Nature 370, 389–391; Stemmer, W. P. (1994) Proc. Natl. Acad. Sci. USA 91, 10747–10751) can be used to generate phage display libraries of VSPβ genes containing random mutations. Since these mutations could alter the structure of VSP, correctly-folded variants can be selected for by their ability to bind a set of monoclonal antibodies recognizing different conformational domains of wild-type VSP. Likewise, correctly-folded variants can be selected by their abilities to homo-heterodimerize. Correctly-folded VSP variants (i.e., those retaining the ability to bind VSP-specific conformational antibodies and homo/heterodimerize) can be selected by phage display technology or screened using a filter lift assay (see methods). Subsequent isolation and sequencing of these variants reveals the tolerated mutations. Amino acid substitutions which do not compromise the VSPβ structure may be good candidates for site-directed methionine substitutions.

In addition to this "random" approach, a method for the "semi-rational" incorporation of methionines into VSP was developed. Although the 3-D structure of VSP is uncertain, secondary structure prediction of the protein (see strategy 2 below) allowed "semi-rational" methionine substitutions. Analysis of VSPβ homology with tomato acid phosphatase, a protein with 45% identity to VSPβ, as well as other homologs allowed additional methionine substitutions (see strategy 3 below). Two methods were designed by which to introduce these substitutions. The first method involves DNA shuffling in the presence of excess methionine-encoding oligos which, by protein secondary structure predictions, are complementary to multiple regions of the VSPβ gene corresponding to protein loops. The second novel method employed overlap PCR of segments of the VSPβ gene corresponding to protein loops which have been amplified with the methionine-encoding oligos. The methods by which these oligos (corresponding to, for example, twenty-two different methionine substitutions) are introduced into VSPβ result in the production of a library of phage-displayed VSP variants; theoretically each variant contains zero to twenty-two additional methionines. Subsequent phage display and biopanning of these libraries against VSP-specific monoclonal antibodies can lead to the identification of residues in VSP which can accommodate methionine without significantly altering the structure of the protein.

A VSPβ mutant library was made by error prone PCR methodology (see below). From this pool of mutants, a filter lift assay (see methods) was performed to identify properly-folded mutant VSPβ based on the ability to bind to either VSPα or a VSP-specific monoclonal antibody. Using VSPα as the antigen in a filter lift assay (FIG. 5) 18 out of 50 VSPβ variants tested bound VSPα. Sequence analysis of 15 of these variants revealed a total of 84 point mutations which correlate with 58 AA substitutions and 25 silent mutations. Together these represent 51 different residues within the 218 AA VSPβ.

2. Secondary Structure Prediction

Structural features of a protein are very important for proper folding. Sequence analysis tools such as the GCG (Wisconsin Sequence Analysis Package, Genetic Computer Group, University Research Park, 575 Science Drive, Madison, Wis.) and PC/GENE (Oxford Molecular Group, 2105 S. Bascom Avenue, Suite 200, Campbell, Calif.) were used to analyze the VSPβ sequence for secondary structure features such as helices, sheets and turns and for determining whether a particular stretch of amino acids might reside on the surface of the protein. Residues on the surface of a protein would likely tolerate substitution more readily than a buried residue without compromising the structure of the protein. Using these algorithms, numerous predicted turns and surface regions of the protein were identified. Many of these regions are expected to tolerate methionine substitution. For example residues at positions 25, 30, 32, 37, 44, 65, 67, 102, 121, 130, 160, 163, 164, 169, 198, 202, and 207 in VSPβ occur in predicted turn regions and were substituted with Met (Table 1).

3. Homology Comparison

Over time, nature has tested the tolerance of protein residues to substitution, and this is exemplified in the sequences of proteins such as globins and cytochromes from several different species, members of which have the same fold (Hampsey, M. D., Das, G., Sherman, F. (1988) FEBS Lett. 231,275; Bashford, D., Chothia, C. & Lesk, A. M. (1987) J. Mol. Biol. 196, 199, Lesk, A. M. & Chothia, C. (1980) J. Mol. Biol. 136,225). These and other studies have demonstrated that hydrophobic residues (such as Ala, Sys, Val, Ile, Leu, Met, Phe and Trp) almost always occur in the hydrophobic core of the protein and that they may substitute for each other without undue perturbation of the structure (Bowie, J. U., Reidhaar-Olson, J. F., Lim. W. A., & Sauer, R. T. (1990) Science 247, 1306–1310; Baldwin, E. P., & Matthews, B. W. (1994) Curr. Opin. Biotech. 5, 396–402). Indeed, it has been observed that "Residue positions that can accept a number of different side chains, including charged and highly polar residues, are almost certain to be on the protein surface. Bowie et al. (1990) Science 247:1306–1310, have Residue positions that remain hydrophobic, whether variable or not, are likely to be buried within the structure". Furthermore, in a recent comprehensive analysis of substitution patterns in several databases of multiply aligned protein sequences, Ladunga and Smith (1997) Prot. Eng. 10:187–196, have concluded that the overall emphasis is on the preservation of three dimensional structure of the protein and that residues that substitute for each other in related sequences do so by conserving the physico-chemical properties of the residue and the folding of the protein. In the case of VSP, this evolutionary data was utilized by comparing the homology of VSPβ with six homologous proteins (FIG. 1).

Amino acids that are critical to the function and/or folding of a protein would be expected to be conserved over time. For example, cysteine 7 and 29 are conserved in all seven of the homologous proteins aligned in FIG. 1. These residues are involved in forming a disulfide bond that may be expected to be of importance to the structure of the protein. In summary, analysis of the VSPβ sequence with its homologs led to the identification of 31 residues (out of 218 amino acids) that in all liklihood will tolerate methionine substitution.

Engineering VSPβ for Increased Methionine
Rational

Wild-type VSPβ contains 1.4% methionine. Using the three strategies described, three different VSPβ variants with increasing amounts of methionine have been proposed (9.6%, 14.2%, 17.9%, FIG. 2). The overall amino acid composition in each of these constructs is presented in Table 2. Construct VSPβ-met20 (14.2% Met) contains the same 18 Met substitutions as the VSPβ-met10 derivative plus an additional 11 Met residues. Likewise VSPβ-met30 contains the same 29 Met substitutions as VSPβ-met20 plus an additional 7 Met residues. Mutational analysis of VSPβ resulted in the mutation of 51 different amino acids out of the 218 amino acid protein. Although these mutations were not methionine substitutions, the types of tolerated substitutions were examined for their relevance to substitution to a hydrophobic amino acid. For example, positions 50, 67, 93, 127, 150, and 164 tolerated mutation to a hydrophobic amino acid (Table 1). Therefore, it is possible that this same position might tolerate substitution to methionine. Positions 62, 67, 76, 127, and 164 are hydrophobic amino acids in VSPβ—wild type. The observation that these positions tolerate substitution at all suggests they would more readily tolerate a conservative substitution (i.e., hydrophobic amino acid to hydrophobic amino acid, Table 1). Since residues 32, 50, 65, 67, 76, 93, 127, 150, 160, and 202 allowed non-conservative mutations, it is possible that these positions would tolerate mutation to methionine (Table 1). In every case where these amino acids were not changed from or to a hydrophobic amino acid in the mutational analysis, at least one additional strategy (i.e., secondary structure or homology comparison) was used to rationalize methionine substitution at the particular position. In summary, in the three methionine enriched constructs proposed, 12 residues (out of a total of 36) were selected based at least in part on mutational analysis. More specifically, mutational analysis indicated 6/18 methionine substitutions in construct VSPβ-met10, 9/29 in construct VSPβ-met20, and 12/36 in VSPβ-met30 (Table 1). As mentioned, mutational analysis revealed 51 different positions within VSPβ tolerant to substitutions. Interestingly, 25/51 (49%) of the mutated positions are located in regions of the protein predicted to exist as turns, 17/51 (33%) in helices, and 9/51 (18%) in p-sheets. These percentages are significantly different from the predicted distribution of turns (25%), helices (25%) and β-sheets (50%), indicating that, as expected, the regions of the protein most likely to be located on the surface (e.g., turns) can more readily accommodate substitutions without compromising the structure of the protein. This suggests the importance of protein secondary structure prediction as one of the strategies utilized in the identification of residues for methionine substitution.

Since protein turns are generally more surface-exposed regions that do not contribute greatly to the overall structure of the protein, these regions were targeted for methionine substitution. In fact, out of the 36 positions selected for methionine substitution, 17 (47.2%) are predicted to occur in turns. In contrast, because β-sheets are protein structural elements that generally occur at the core of the protein, these regions were avoided in selecting sites for methionine substitution. Out of the 36 positions selected for methionine substitution, only 7 (19.4%) are predicted to occur in β-sheets. Nearly all of these residues were hydrophobic in wild-type VSPβ and were thought to tolerate methionine based upon the homology comparison strategy. Additionally, 12 (33.3%) of the residues selected for methionine substitution in the three constructs are predicted to occur in helices. In summary, secondary structure prediction is the strategy responsible, at least in part, for 17/36 sites targeted for methionine substitution. More specifically, secondary structure prediction correlates with the selection of 7/18, 14/29, and 17/36 amino acids for methionine substitution in constructs VSPβ-met10, VSPβ-met20, and VSPβ-met30, respectively (Table 1).

Homology comparison was a very informative strategy in selecting residues that might tolerate methionine substitution. Accordingly, methionine substitutions in VSPβ were made by adhering to the following rules and also summarized in Table 1:

(a) Conserved residues (shown in FIG. 1) were defined as those residues occurring in more than 5 of the 7 homologs. These were not targeted for substitution. The exceptions were: at residue numbers 19, 37, 146 and 179 (one of the homologs contained a methionine residue); at positions 67, 80, 130 and 169 (conserved hydrophobic amino acid exchanges observed in at least one sequence) and at position 50 (non-conservative changes from Asn to Ser/Cys in two sequences).

(b) Similarly, non-conserved positions were defined as those containing residues with different side-chain properties. Several positions in VSPβ were correlated with non-conservative amino acids in the homologs (e.g., 5, 19, 25, 30, 37, 44, 60, 62, 65, 67, 72, 76, 80, 90, 97, 102, 121, 127, 130, 135, 142, 146, 150, 164, 169, 179, 189, 198, 202, 207, and 217). Such residues likely reside on the surface/turns of the protein and were considered less important for protein function and/or folding and therefore targeted for substitution with methionine.

(c) In addition, some positions in which at least one other hydrophobic amino acid was observed among homologs (e.g., 0, 1, 2, 3, 4, 5, 6, 7, 8, 9, 10, 12, 13, 14, 15, 16, 17, 18, 19, 20, 21, 25, 30, 37, 44, 60, 62, 65, 67, 72, 76, 90, and 97) were also expected to tolerate substitution to the hydrophobic amino acid methionine. Exceptions to this were cases in which the hydrophobic amino acid was completely conserved in all 6 homologs (e.g., Val 49, Leu 77, Leu 110, Leu 114, Leu 145, Ile 157, Leu 158, Ile 186, Val 187, Leu 197 and Leu 210). In these cases, the possibility that the specific hydrophobic amino acid in the wild-type protein may be playing a role critical for the proper structure and/or function of the protein was considered. To avoid disturbing this possible role, the substitution of any residue that is completely conserved in all 6 homologs examined was not proposed.

(d) Six residues within VSPβ that were expected to tolerate methionine substitution were identified based on the presence of methionine in analogous positions in homologs (e.g., 19, 37, 44, 146, 179, and 202).

A few additional considerations were observed in selecting amino acids that might tolerate methionine substitution.

(e) We avoided altering histidine residues due to their potential importance in phosphatase activity of VSPβ (Table 2 and DeWald, D. B., Mason, H. S., & Mullet, J. E. (1992) J. Biol. Chem. 267, 15958–15964).

(f) Since VSPβ is a glycoprotein, this feature may be important for the stability and/or function of the protein, substitution of potential glycosylation sites was avoided (e.g., Asn 94).

(g) In addition, wherever possible, charged residues such as Lys, Arg, Glx, Asx were left untouched to preserve the hydrophobic/hydrophilic balance of the protein (Table 2 and FIGS. 3A–D). While wild-type VSPβ has a calculated charge of −4, VSPβ-met10, VSPβ-met20, and VSPβ-met30 have calculated charges of −7,−7, and −5, respectively.

As a strategy, homology comparison facilitated, at least in part, the selection of 31/36 of the residues proposed formethionine substitution. These selections correlate with 18/18, 28/29, and 31/36 residues for constructs VSPβ-met 10, VSPβ-met20, and VSPβ-met30, respectively (Table 1).

Several of the amino acids selected for methionine substitution in the three constructs resulted from more than one strategy. In fact, the majority (20/36) of the targeted residues resulted from at least two strategies, with a few (4/36) resulting from all three strategies.

Experimental Results

A synthetic gene for methionine enriched VSPβ-met10 has been constructed. This synthetic gene differs from wild-type VSPβ in that it encodes eighteen additional methionines (FIG. 4). Also, a few silent point mutations were introduced into this construct to create unique restriction sites. To test whether the proposed VSPβ-met10 gene was correctly folded, the construct was cloned into the phagemid vector pCANTAB-5E and the abilities of the expressed proteins to bind VSP-specific conformational monoclonal antibodies in a filter lift assay were compared. The results indicate that the VSPβ-met10 gene was able to bind the same antibodies as wild-type VSPβ. This suggests that VSPβ-met10 may be correctly folded in an *E. coli* secretion system.

Together, these interdisciplinary approaches should not only result in the engineering of a nutritionally-enhanced VSP, but also provide clues to the structure of VSP—a protein for which no 3D structure is available. This approach is applicable to any protein of interest.

Methods

1. Random Mutation of Vegetative Storage Protein (VSPβ) by Error-Prone PCR

The VSPβ gene was amplified by mutagenic PCR using primers flanking the gene.

1 cycle (1 min. at 95° C., 1 min. at 51° C., 3 min. at 72° C.)
16 cycles (1 min. at 91° C., 1 min. at 51° C., 3 min. at 72° C.)
1 cycle (1 min. a 91° C., 1 min. at 51° C., 5 min. at 72° C.)

The products of these four reactions were pooled, and the band corresponding to the mutagenized VSPβ gene was purified from an agarose gel, digested with SfiI and NotI and cloned into the phagemid vector pCANTAB-5E.

2. Filter Lift Assay

Fifty *E. coli* colonies containing randomly mutated VSPβ genes were picked as small patches to an SB agar plate containing glucose and ampicillin. Patches were allowed to grow overnight at 37° C. and were then transferred to a nitrocellulose filter. On the surface of an SB agar plate containing ampicillin and IPTG, this filter was placed on top (cell-side up) of a separate blocked filter to which the antigen (e.g., VSPα) had been coated. During an overnight incubation at 30° C., the cells expressed the VSPβ variant they encoded. These proteins were able to diffuse through the top filter and, if correctly folded, bind the antigen-coated filter below. The next day, the antigen-coated filter was washed with PBS-0.05% Tween™ and incubated with HRP/anti-e tag conjugate. Since the VSPβ mutants are cloned into the pCANTAB-5E vector which fuses a C-terminal epitope tag (e-tag) to the VSPβ protein variants, bound proteins were detected by this antibody in combination with enhanced chemiluminescence detection.

TABLE I

Proposed Methionine Substitutions

| VSPβ position | Mutational Analysis[1] | Secondary Structure[2] | Original A.A. hyrophoibic? | Met in homolog?[3] | # homologs hydrophobic[4] |
|---|---|---|---|---|---|
| Construct 1 (9.6% Met) | | | | | |
| 5 | Y | — | — | Y | — | 3 of 6 |
| 19 | I | — | — | Y | Y-Ar. VSP | 6 of 6 |
| 30 | V | — | T | Y | — | 2 of 6 |
| 37 | I | — | T | Y | Y-T. phos | 6 of 6 |
| 44 | I | — | T | Y | Y-T. phos | 1 of 6 |
| 60 | R | — | — | — | — | 5 of 6 |
| 62 | V | V-A | — | Y | — | 6 of 6 |
| 67 | I | I-T, L | T | Y | — | 5 of 6 |
| 72 | I | — | — | Y | — | 6 of 6 |
| 76 | V | V-G | — | Y | — | 5 of 6 |

| Reaction 1 | Reaction 2 | Reaction 3 | Reaction 4 |
|---|---|---|---|
| 10 mM Tris-HCl | 10 mM Tris-HCl | 10 mM Tris-HCl | 10 mM Tris-HCl |
| 50 mM KCl | 50 mM KCl | 50 mM KCl | 50 mM KCl |
| 9.5 mM MgCl2 | 9. mM mgCl2 | 9. mM mgCl2 | 9. mM mgCl2 |
| 0.5 mM MnCl2 | 0.5 mM MnCl2 | 0.5 mM MnCl2 | 0.5 mM MnCl2 |
| 5 µg/ml BSA | 5 µg/ml BSA | 5 µg/ml BSA | 5 µg/ml BSA |
| 600 pmol VSP template | 600 pmol VSP template | 600 pmol VSP template | 600 pmol VSP template |
| 0.1 µm each primer | 0.1 µm each primer | 0.1 µm each primer | 0.1 µm each primer |
| 2 mM dATP | 200 µM dATP | 200 µM dATP | 200 µM dATP |
| 200 µM dCTP | 2 mM dCTP | 200 µM dCTP | 200 µM dCTP |
| 200 µM dGTP | 200 µM dGTP | 2 mM dGTP | 200 µM dGTP |
| 200 µM dTTP | 200 µM dTTP | 200 µM dTTP | 2 mM dTTP |
| 2 Units Taq Pol | 2 Units Taq Po | 2 Units Taq Pol | 2 Units Taq Pol |

TABLE I-continued

Proposed Methionine Substitutions

| VSPβ position | Mutational Analysis[1] | Secondary Structure[2] | Original A.A. hyro-phoibic? | Met in homolog?[3] | Homology Comparison # homologs hydro-phobic[4] |
|---|---|---|---|---|---|
| 121 | L | — | T | Y | — | 6 of 6 |
| 127 | I | I-T, L | — | Y | — | 3 of 6 |
| 146 | K | — | — | — | Y-T. phos | 1 of 6 |
| 164 | I | I-V | T | Y | — | 3 of 5 |
| 179 | L | — | — | Y | Y-T. phos | 6 of 6 |
| 189 | I | — | — | Y | — | 2 of 6 |
| 202 | R | R-G, T | T | — | Y-T. phos | 1 of 6 |
| 217 | I | — | — | Y | — | 5 of 6 |
| Construct 2-additional substitutions (14.7% Met) | | | | | |
| 32 | P | P-Q | T | — | — | 0 of 6 |
| 65 | N | N-S | T | — | — | 3 of 6 |
| 90 | V | — | — | Y | — | 2 of 6 |
| 97 | L | — | — | Y | — | 1 of 6 |
| 102 | V | — | T | Y | — | 5 of 6 |
| 130 | L | — | T | Y | — | 6 of 6 |
| 135 | L | — | — | Y | — | 1 of 5 |
| 150 | F | F-S, I, L | — | — | — | 3 of 6 |
| 169 | L | — | T | Y | — | 5 of 6 |
| 198 | T | — | T | — | — | 5 of 6 |
| 207 | T | — | T | — | — | 3 of 6 |
| Construct 3-additional substitutions (17.9% Met) | | | | | |
| 25 | I | — | T | Y | — | 6 of 6 |
| 50 | N | N-I | — | — | — | 0 of 6 |
| 80 | I | — | — | Y | — | 6 of 6 |
| 93 | F | F-V | — | — | — | 0 of 6 |
| 142 | E | — | — | — | — | 3 of 6 |
| 160 | D | D-Y | T | — | — | 0 of 6 |
| 163 | L | — | T | Y | — | 0 of 6 |

[1]Amino acid substitution observed in the mutational analysis. For example, at position 62, a valine to alanine substitution was observed.
[2]"T" indicates turn predicted by secondary structure analysis of VSPβ.
[3]"Y" indicates the presence of Methionine in the designated VSP homolog.
[4]Includes only aliphatic hydrophobic amino acids such as Leu, Ile, Val, and Met.

TABLE 2

Amino Acid Composition of VSPβ-WT and Methionine-Enriched Variants

| | VSPβ | VSPβ-Met10 | VSPβ-Met20 | VSPβ-Met30 |
|---|---|---|---|---|
| Ala | 13 | 13 | 13 | 13 |
| Arg | 11 | 9 | 9 | 9 |
| Asn | 14 | 14 | 13 | 12 |
| Asp | 11 | 11 | 11 | 10 |
| Cys | 2 | 2 | 2 | 2 |
| Gln | 6 | 6 | 6 | 6 |
| Glu | 19 | 19 | 19 | 18 |
| Gly | 13 | 13 | 13 | 13 |
| His | 7 | 7 | 7 | 7 |
| Ile | 14 | 6 | 6 | 4 |
| Leu | 20 | 18 | 13 | 12 |
| Lys | 15 | 14 | 14 | 14 |
| MET | 3 (1.4%) | 21 (9.6%) | 32 (14.7%) | 39 (17.9%) |
| Phe | 12 | 12 | 11 | 10 |
| Pro | 9 | 9 | 8 | 8 |
| Ser | 13 | 12 | 12 | 12 |
| Thr | 10 | 10 | 9 | 9 |
| Trp | 3 | 3 | 3 | 3 |
| Tyr | 12 | 12 | 12 | 12 |
| Val | 11 | 7 | 5 | 5 |
| Total | 218 | 218 | 218 | 218 |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for altering the composition of VSPβ as set forth in SEQ ID NO:1, said method comprising:
   a) introducing amino acid changes into SEQ ID NO:1 to create an engineered VSPβ having increased nutritional value, wherein said amino acid changes increase levels of at least one nutritionally essential amino acid so that nutritionally essential amino acids are increased to represent at least 5%–10% of the total amino acid content of the engineered VSPβ; and
   b) assessing the conformation of said engineered VSPβ based on its ability to bind with a set of antibodies, wherein said set of antibodies bind SEQ ID NO:1.

2. The method of claim 1, wherein at least one of said nutritionally essential amino acids is methionine.

3. The method of claim 1, wherein said amino acid changes are introduced into predetermined sites.

4. The method of claim 3, wherein said predetermined sites are determined by secondary structure prediction or homology comparison.

5. The method of claim 1, wherein said amino acid changes are introduced at random.

6. The method of claim 5, wherein said amino acid changes are produced by mutagenic PCR or DNA shuffling, wherein said mutagenic PCR or DNA shuffling is optionally used in combination with phage display methodology.

* * * * *